United States Patent
Betz et al.

(10) Patent No.: US 6,287,308 B1
(45) Date of Patent: Sep. 11, 2001

(54) METHODS AND APPARATUS FOR FUSIONLESS TREATMENT OF SPINAL DEFORMITIES

(75) Inventors: Randall Betz, Langhorne, PA (US); Michael C. Sherman; Troy Drewry, both of Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/350,876

(22) Filed: Jul. 9, 1999

Related U.S. Application Data

(63) Continuation-in-part of application No. 08/892,604, filed on Jul. 14, 1997, now Pat. No. 5,951,553.

(51) Int. Cl.⁷ .................................................. A61B 17/56
(52) U.S. Cl. ............................................................. 606/61
(58) Field of Search .................................. 606/61, 60, 64, 606/63, 67–68, 72–73, 75, 105, 219; 623/17.11, 17.16, 18.11; 411/429, 426

(56) References Cited

U.S. PATENT DOCUMENTS

| | | |
|---|---|---|
| 2,485,531 | 10/1949 | Dzus et al. . |
| 4,041,939 | 8/1977 | Hall . |
| 4,047,524 | 9/1977 | Hall . |
| 4,289,123 | 9/1981 | Dunn . |
| 4,658,809 | 4/1987 | Ulrich et al. ............................ 606/64 |
| 5,246,443 | 9/1993 | Mai . |
| 5,395,372 | 3/1995 | Holt et al. ............................... 606/61 |
| 5,562,735 | 10/1996 | Margulies . |
| 5,569,246 | * 10/1996 | Ojima et al. ............................ 606/61 |
| 5,620,443 | 4/1997 | Gertzbein et al. ...................... 606/61 |

(List continued on next page.)

FOREIGN PATENT DOCUMENTS

| | | |
|---|---|---|
| 26 49 042 | 10/1976 | (DE) . |
| 0 545 830 A1 | 11/1992 | (EP) .................................. A61F/2/08 |
| 1424826 | 9/1988 | (RU) . |

OTHER PUBLICATIONS

Publication entitled *Treatment of intra–articular fractures with shape memory compression staples*, "Injury", 1993, pp. 651–655, by K.R. Dai et al.

*Spinal Osteotomies in Adult Scoliosis Surgery*, John P. Kostuik, M.D., Lumbosacral and Spinepelvic Fixation, 1996.

Primary Examiner—Olik Chaudhuri
Assistant Examiner—Vikki Hoa B. Trinh
(74) Attorney, Agent, or Firm—Woodard, Emhardt, Naughton, Moriarty & McNett

(57) ABSTRACT

The treatment and correction of spinal deformities, such as scoliosis, is accomplished without the need for fusion of the intervertebral disc space. A surgical technique is provided in which opening and closing osteotomies are created in the affected vertebrae. Correction devices are provided which hold the osteotomies in either their closed or open orientations. The correction devices include bone-piercing anchors, some in the form of staples, holding the vertebral body on opposite sides of the body to retain the osteotomies in their desired orientation. In the opening osteotomies, the correction devices include a wedge member that is disposed within the opened wedge osteotomy and in contact with the vertebral body. The correction devices also include connection members which can be used to engage the devices to an elongated member spanning the spine, such as a spinal rod or a metal or non-metal cable or tether. Once bone union has occurred in the instrumented vertebrae, the spinal rod or cable or tether can be disconnected from the correction devices and removed from the patient. In another aspect of the invention, curvature deformities in two planes can be corrected using the same techniques and devices.

46 Claims, 17 Drawing Sheets

U.S. PATENT DOCUMENTS

| | | |
|---|---|---|
| 5,645,599 | 7/1997 | Samani . |
| 5,713,899 | 2/1998 | Marnay et al. ............... 606/61 |
| 5,728,127 | 3/1998 | Asher et al. . |
| 5,738,685 | 4/1998 | Halm et al. ............... 606/61 |
| 5,741,254 * | 4/1998 | Henry et al. ............... 606/61 |
| 5,928,231 * | 7/1999 | Klein et al. ............... 606/60 |

* cited by examiner

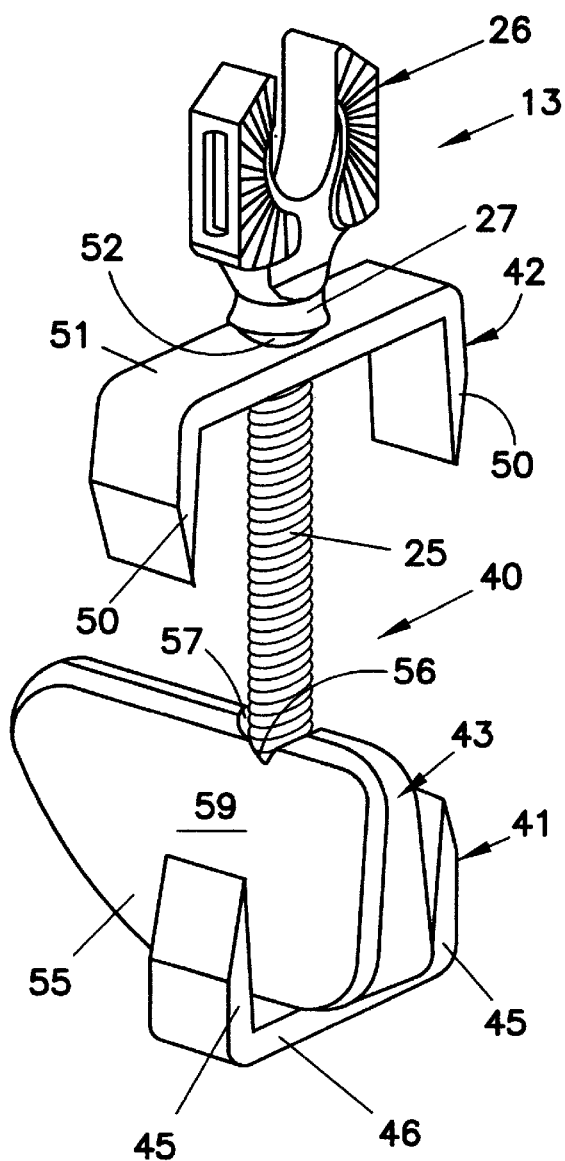
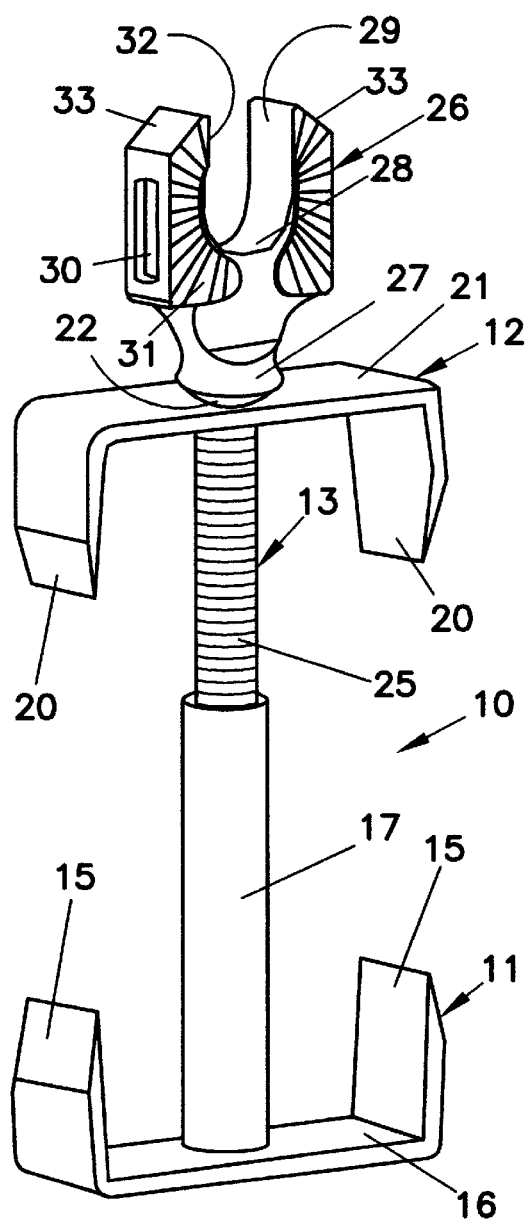
FIG. 2
FIG. 1

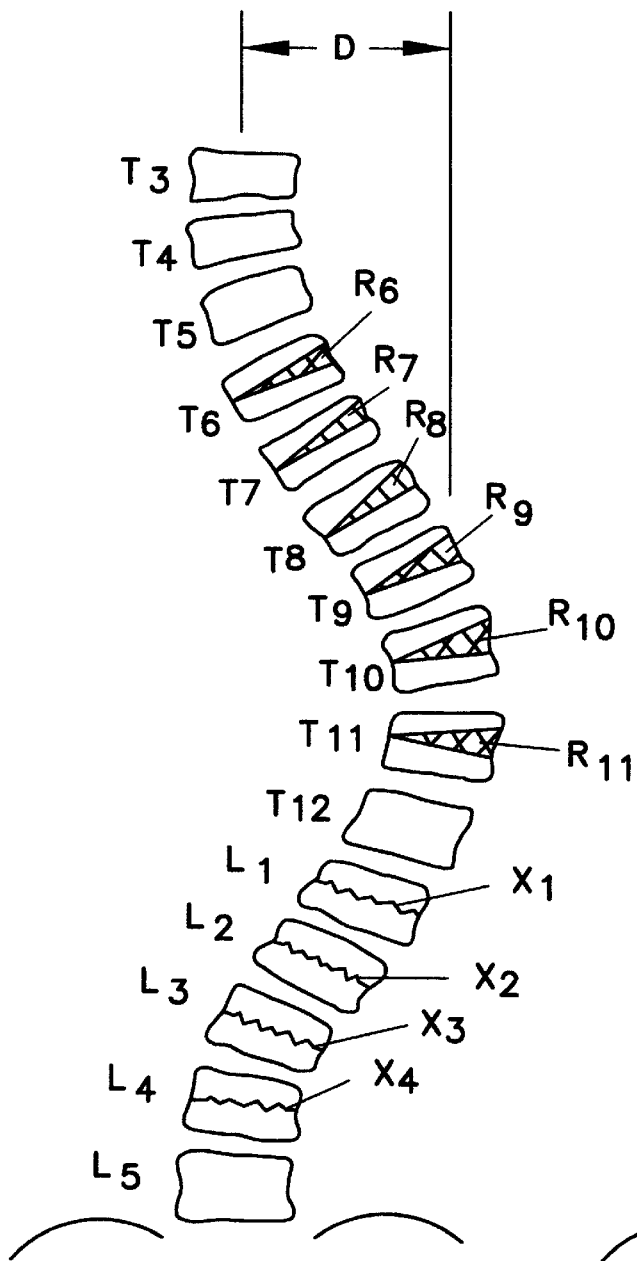
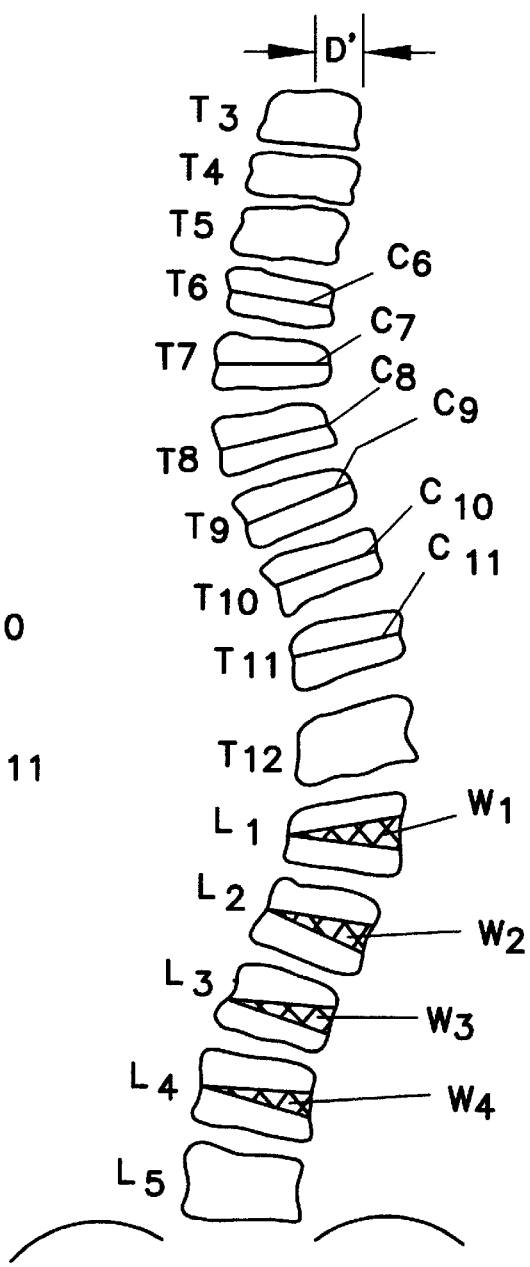
FIG. 11
FIG. 12

METHODS AND APPARATUS FOR FUSIONLESS TREATMENT OF SPINAL DEFORMITIES

This patent application is a continuation-in-part of application Ser. No. 08/892,604, filed Jul. 14, 1997 now U.S. Pat. No. 5,951,553.

BACKGROUND OF THE INVENTION

The present invention concerns instrumentation and techniques for the treatment of spinal deformities. In particular, the inventive methods and devices accomplish this treatment without the need for fusion of the spine.

Surgical intervention for the treatment of injuries to, and deformities of the spine is approaching its first century. Nevertheless, the field of spinal surgery was not significantly advanced until the development of the hook and rod system by Dr. Harrington in the early 1950's. Dr. Harrington developed this system in Houston when he began care of children with progressive neuromuscular scoliosis secondary to polio. Until that time, the progressive scoliosis had been treated with external casts, which themselves yielded unacceptably high complication rates. After a decade of development, the hook and rod system evolved into the form that is known today as the Harrington Instrumentation.

The original primary indication for use of Harrington Instrumentation was in the treatment of scoliosis. Scoliosis is a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions.

Early techniques for correction of scoliosis utilized a halo-traction device. In this technique, a halo is fixed to the skull and a vertical force is applied to the spine through the skull. In a halo-femoral traction approach, the patient is supine and traction forces are applied through a halo and a femoral pin. In a halo-gravity traction procedure, the patient sits in a wheelchair and a suspended weight applies a vertical force through the halo. In halo-pelvic traction, a pelvic ring is affixed to the patient and a series of threaded rods connect the cranial halo to the pelvic ring to apply an adjustable force separating the two rings. In procedures using the halo, the patient is either immobile or severely restricted in mobility.

To avoid the need for halos, various rod-based systems have been developed. Of course, the original rod system for correction of scoliosis is the Harrington System which utilized threaded and notched rods. In particular, a typical Harrington System utilizes a notched distraction rod and at least one threaded compression rod, with the distraction and compression rods being applied to the concave and convex portions of the curvature, respectively. In some procedures, a single distraction rod spans across several thoracic and lumbar vertebrae. The threaded compression rods are then used to stabilize the rod fixation. In other approaches, the compression rod spans across the convex portion of the curve, such as between $T_6$ and $L_2$. In a Harrington procedure, a hook placed at the notched end of the distraction rod can be progressively advanced toward the cranial end of the rod to progressively correct the spinal deformation. At the same time, hooks engaged to the threaded compression rods can be drawn together on the convex side of the curvature to assist in the correction and to stabilize the instrumented spine.

In an additional step of the Harrington procedure, once the spine has been substantially corrected, transverse stabilization can be added between the two rods extending on opposite sides of the spine. Importantly, for long term stability, bone graft is placed along the instrumented vertebral levels to achieve fusion along that portion of the spine.

One drawback commonly associated with the Harrington System is that the rods are completely straight. As a result, patients in which a Harrington System has been used to correct a scoliosis condition have been left with the so-called flat-back syndrome. Specifically, in correcting the lateral curvature of the spine, the normal sagittal plane curvature is eliminated by the presence of a completely straight rod. In some cases, it has been found that the patient is better off retaining the scoliotic curvature than enduring the complications associated with flatback syndrome. Another drawback is the requirement of bracing and casting.

To address these problems, subsequent rod-based systems have relied upon pre-bent spinal rods and multiple fixation sites. Specifically, the rods are bent to the normal thoracic kyphosis and lumbar lordosis in the sagittal plane. One such system is the Luque segmental spinal instrumentation. In the early 1980's, Dr. Luque pioneered a technique for segmental correction of abnormal spinal curvatures in which wires were used to affix vertebral levels to a pre-bent rod. These sublaminar wires are used to help draw the vertebrae toward the rod and ultimately to hold the vertebrae in position. In one approach using Luque instrumentation, a unit rod is provided which utilizes a single rod anchored at its ends to the ilium and bent at its cranial end so that two halves of the rod are oriented on opposite sides of the spinal column. The unit rod can then be used as a lever to straighten the spine, after which Luque sublaminar wires are used to fix the vertebrae to the unit rod.

As with the Harrington System, the final step of the Luque Instrumentation is frequently fusion of the instrumented spinal segments. There have been suggestions for instrumentation without fusion to correct scoliosis in younger patients, this technique was believed to permit further spinal growth. However, the results of this instrumentation without fusion were not very promising and led to certain complications, including loss of correction, reduced spinal growth and an unacceptable rate of instrumentation failure.

In yet another rod-based instrumentation system pioneered by Dr. Cotrel in France, a pre-curved rod is engaged to the vertebrae at the concave side of the abnormal curvature. The rod is then rolled about its axis to derotate the scoliotic curvature and at the same time provide the instrumented segments with the normal sagittal plane curvature. For instance, in the correction of thoracic lordoscoliosis, rolling of a pre-curved rod not only derotates the curvature in the coronal plane, it also transforms that scoliotic curvature into a physiological thoracic kyphosis. The rod is held to the vertebrae by a series of hooks, which are ultimately fixed to the rod once the derotation process is complete. To ensure a stable correction, an additional rod is added on the opposite side of the spinous process from the first rod. Members for transversely connecting the two rods create a rigid scaffold are attached. Again, in this procedure, bone chips are placed along the instrumented vertebrae to achieve fusion at the instrumentation site.

Other rod-based systems have been developed over the last several years that accomplish similar correction of spinal deformities, such as scoliosis. For example, the TSRH® Universal Spine System of Danek Medical, Inc. and the ISOLA® Spine System of AcroMed Corp. can be instrumented to the spine to correct various types of spinal deformities. In all of these rod-based systems, the spinal rods are permanently fixed to the patient's spine. Of course, once fusion of all the instrumented levels has occurred, the original instrumentation is largely superfluous.

Other techniques that have been developed for correction of spinal deformities are performed anteriorly from the convex side of the abnormal curvature. In this technique, the intervertebral discs are removed and an osteotomy spreader is used to separate the adjacent vertebrae, thereby realigning the vertebral bodies in the coronal plane. A rod is attached to the spine via screws to maintain the correction. Fusion material, such as bone chips, are inserted into the widened intervertebral disc spaces to ultimately achieve fusion at those vertebral levels. Immobilization using an external cast or brace can be utilized while fusion is occurring.

A related technique involves Dwyer instrumentation that utilizes a flexible cable. In this technique, the cable is connected to the affected vertebrae on the convex side of the curvature. The cable is then shortened, thereby applying compression to the convex side of the curvature. Once the curvature has been corrected using the Dwyer cable, ancillary instrumentation, such as a Harrington rod, can be added for fixing and stabilizing the spine. In the Dwyer instrumentation, Dwyer clamps are pressed into the vertebral bodies to provide a seat for the insertion of Dwyer screws. The Dwyer screws define a channel through which the Dwyer cable can pass to perform the compression and ultimately the derotation of the abnormal curvature.

A similar approach is taken using Zielke instrumentation, except that the Dwyer cable is replaced by a pre-bent threaded rod. Application of the compressive forces to reduce the convex side of the curvature occurs by threaded nuts along the rod to translate the bone screws engaged to the vertebrae. Failed fusion because of residual deformity can be corrected by using posterior osteotomies which are closed and anterior wedges which are usually open. Following mobilization of the spinal segments by the osteotomies, then the spinal deformity can be corrected with instrumentation and then re-fused to maintain the correction.

While many techniques and instrumentation have been developed for the correction of spinal deformities, none of which we were aware prior to our invention, had been devised that could achieve the necessary correction without fusion of the instrumented vertebral levels. Moreover, some of the techniques resulted in an undesirable flat-back syndrome in which the normal sagittal plane curvature is eliminated. In addition, the prior systems greatly restrict the patient's normal mobility, and some restrict the growth of the spine. In the latter instance, some of the spinal instrumentation is not acceptable for use in younger patients.

A need exists for a technique and system to correct spinal deformities without the necessity of fusing the corrected vertebral segments. A need also exists for a system and technique that can accomplish this correction with minimal long-term invasion of the patient.

SUMMARY OF THE INVENTION

In order to address these unmet needs, a method and instrumentation are provided for correction of spinal deformities without the need for fusion of the corrected segments. In one aspect of the invention, a surgical technique is provided in which osteotomies are closed on the convex side of the curvature deformity and opened on the concave side of the curvature. Mechanical wedges are engaged within the open wedge osteotomies on the concavity of the curvature. The vertebral bodies will heal and form a unified body at the location of the closed osteotomies. In this manner, the normal coronal plane position of the spine is restored by elimination of the curvature deformity.

In a further aspect of the technique, the orientation of the opening or closing wedge osteotomies can be predetermined to achieve a normal curvature in the sagittal plane and normal spinal orientation in the coronal plane. For example, the addition of mechanical wedges into opening wedge osteotomies in the lumbar spine can be used to eliminate an abnormal lateral curvature while restoring the normal lordotic curvature of the lumbar vertebrae.

In a further aspect of the technique, connection elements or fasteners are engaged to each of the vertebrae in which an osteotomy has been performed. The connection element can then be engaged to an elongated member, such as a spinal rod, that has been pre-bent to the adjusted spinal curvature. The longitudinal member stabilizes the spine as the closing osteotomies heal and the mechanical wedges become integrated into the vertebrae having the opening wedge osteotomies. In this manner, the intervertebral discs are maintained intact. Moreover, and perhaps most significantly, none of the vertebral levels are fused together. Once the vertebral bodies have completely healed, the longitudinal member can be removed. With this feature of the inventive technique, the normal mobility of the patient's spine is restored since the intervertebral discs are not fused.

In another aspect of the invention, instrumentation is provided that can be used to perform the inventive technique. In one feature of the invention, the instrumentation includes a correction device that includes upper and lower anchors configured to penetrate a single vertebral body at substantially opposite sides of the body. In three illustrated embodiments of the instrumentation, the anchors are in the form of staples. In other illustrated embodiments, the anchors are in somewhat the form of a half staple or an adz. In all illustrated embodiments, a connection element is provided that extends between the upper and lower anchors and through the vertebral body. In one implementation, the connection element includes a threaded shank that engages a mating threaded boss on the lower anchor. In another implementation, the connection element has a threaded shank which is fixed to the lower anchor, and a head portion of the instrumentation is threaded onto the shank. In both implementations, the connection element can be used to provide a compressive force between the upper and lower anchors, thereby retaining their position and engagement with the vertebral body.

In the various implementations, the connection element includes a head portion adjacent the upper anchor. The head portion can be configured for connection to an elongated member used to stabilize the spine. In one embodiment, the head of the connection element is configured to engage an elongated spine rod. In another, it is configured for a spinal tethering function.

In accordance with a further feature of the invention, two types of correction devices can be provided. One correction device is utilized to close the closing wedge osteotomy in a vertebral body. In this correction device, the connection element is used to engage an upper and lower anchor to the vertebral body. In the second correction device, a mechanical wedge is attached to the lower anchor. The second correction device is thus used in maintaining the opened wedge osteotomies on the concavity of the curvature to be corrected. The mechanical wedge member is situated within the open space created by the opening wedge osteotomy.

The anchors, stabilize the opening wedge osteotomy in a closing direction around the mechanical wedge as the vertebral body heals. In some mild cases, adequate correction may be achieved without intervertebral rods, plates, cabling or tethering, and a further embodiment of the invention for such cases, is disclosed.

In accordance with the present invention, a method is provided for correcting spinal deformities without the need for fusion of the spine. A further object of the invention is accomplished by the technique and instrumentation that allows a stabilizing elongated member to be used only temporarily. This aspect provides the benefit that the elongated member, such as the spinal rod, can be removed once the instrumented vertebrae have healed, thereby restoring the normal mobility to the patient's spine.

Another object of the present invention is achieved by aspects of the technique and instrumentation that allows for adjustment of the spinal curvature in both the sagittal and the coronal planes. Still other objects and certain benefits of the invention will be discerned from the following written description of the invention together with the accompanying figures.

BRIEF DESCRIPTION OF THE DRAWINGS

FIG. 1 is a side perspective view of a correction device used in connection with the inventive method for treatment of spinal deformities.

FIG. 2 is a side perspective view of a second type of correction device used in this inventive technique, in which the correction device includes a mechanical wedge member for placement within an opening wedge osteotomy.

FIG. 11 is a schematic representation of a deformed spine and depicting the locations of opening and closing wedge osteotomies.

FIG. 12 is a view of the spine shown in FIG. 11 with the osteotomies opened and closed in accordance with the inventive technique.

DESCRIPTION OF THE PREFERRED EMBODIMENTS

Figure 3:
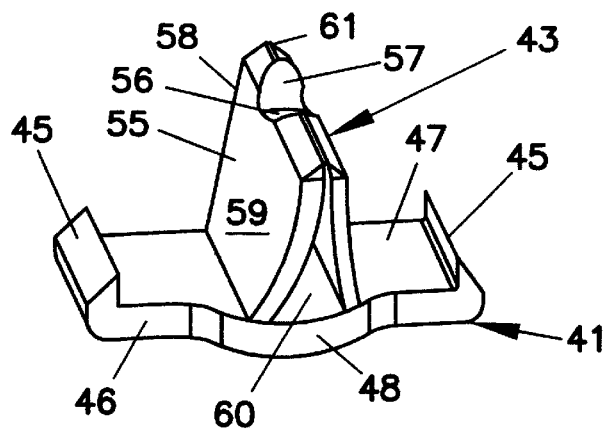
FIG. 3 is a top perspective view of a component of the correction device shown in FIG. 2, particularly showing the mechanical wedge member.
Figure 4:
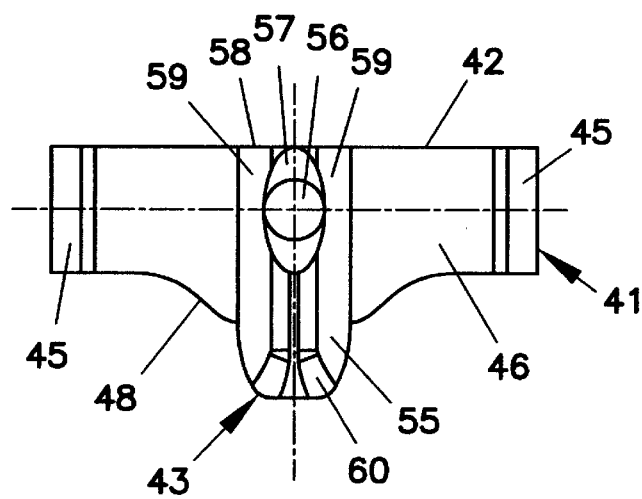
FIG. 4 is a top elevational view of the component shown in FIG. 3.
Figure 5:
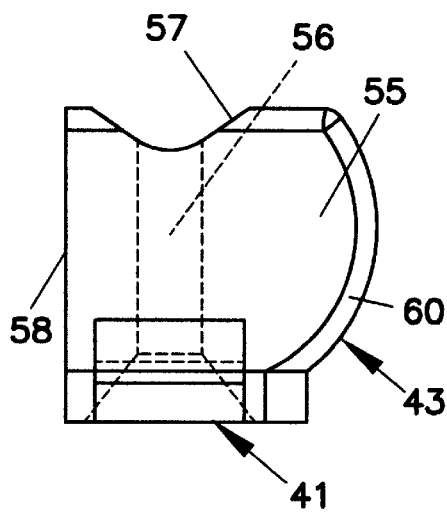
FIG. 5 is an end elevational view of the component shown in FIG. 3.

For the purpose of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

The present invention concerns apparatus and methods for use in the correction of spinal deformities without the need for fusion of adjacent vertebrae. In general terms, the inventive technique involves creating opening and closing osteotomies in the affected vertebrae. Wedges of material are either removed or added to each vertebra as needed to bring the vertebra into a normal spinal alignment. In another aspect of the technique, the opening/closing osteotomies are oriented in the vertebral body so as to effect curvature corrections in both the sagittal and the coronal planes.

The inventive surgical techniques can be accomplished by novel correction devices for a closing osteotomy. One such correction device can include upper and lower staples that are engaged on essentially opposite sides of the vertebral body. A connection member spans between the upper and lower staples to apply a slight compressive force to hold the staples in position. The connection member itself can threadedly engage the lower staple and can include an enlarged head to provide a reaction surface as the threaded shank of the connection member passes through an opening in the upper staple.

The opening osteotomy can be retained by a connection device that includes similar upper and lower staples. In one modification, the opening osteotomy correction device includes a mechanical wedge member attached to the lower staple. The wedge member fits within the osteotomy site to hold the osteotomy open and engage the vertebral body. A similar connection member is provided that can be threaded into the wedge member and that exerts a compressive force at an opening in the upper staple.

In both correction devices, the connection member can include a head portion that is adapted to engage an elongated member spanning the affected vertebrae. In one aspect of the invention, once the opening and closing osteotomies have been perfected by way of the correction devices, the connection members can be engaged to the elongated member, such as a spinal rod, to stabilize the construct. Once bone union is achieved at the osteotomy sites, the spinal rod can be removed to restore the normal motion of the vertebral segments.

With this general description in mind, specific details of the correction devices can be seen with reference to FIGS. 1–10. Looking first at FIG. 1, a correction device 10 is depicted that is used for the closing osteotomy discussed above. The correction device 10 includes a lower bone-piercing anchor 11, an upper bone-piercing anchor 12 and a connection member 13. The lower anchor, in the form of a staple 11 includes a pair of prongs 15 connected to and separated by a base plate 16. The prongs 15 are configured to be pressed into the hard cortical bone of the vertebral body. Such prongs typically include a tapered cross-section to facilitate their insertion and can be of a configuration shown in U.S. Pat. No. 5,395,372, owned by the assignee of the present invention. The lower staple 11 also includes a threaded boss 17 projecting from the base plate 16 in the same direction of the prongs 15. The boss 17 is preferably cylindrical and includes an internally threaded bore.

The upper anchor 12 of the correction device 10 is similarly formed like a staple by upper prongs 20 attached to an upper plate 21. In accordance with the preferred embodiment, the upper staple 12 has a greater width between its prongs 20 than the lower staple 11. In one specific embodiment, the upper staple 12 can have a width of about 2.0 cm between its prongs, while the lower staple 11 can have a width of about 1.5 cm between its prongs 15. Of course, it is understood that the dimensions of the upper staple 12 and lower staple 11 are principally determined by the anatomy of the particular vertebra into which the staples are engaged. In the specific example above, the staples are sized for engagement within a lumbar vertebra. It is further understood that while in the preferred embodiment the upper staple is wider than the lower staple, both staples can have essentially the same width between their prongs.

The next element of the correction device 10 is the connection member 13. The connection member 13 includes an elongated machine threaded shank 25 that bears external threads for mating with the internal threads of the boss 17 of the lower staple 11. In one specific embodiment, the machine threaded shank 25 has a diameter of 0.30 cm with 5-40 UNC 2A machine threads. The internal threads of the boss 17 are similarly configured for mating with the threaded shank 25. The length of the threaded shank 25 is determined by the vertebral anatomy. Preferably, the threaded shank 25 has a length sufficient to span substantially across the vertebral body. For firm engagement of the connection member 13 between the upper and lower staples, it is also preferable that the threaded shank 25 have a length sufficient to extend substantially completely into the threaded boss 17. Likewise, it is also preferable that the threaded boss have a length that is sufficient for a solid threaded engagement between it and the threaded shank. In one embodiment, the threaded boss 17 has a length that is greater than half the length of the threaded shank 25. In a specific embodiment, the threaded shank 25 can have a length of about 45 mm, while the threaded boss 17 of the lower staple 11 has a length of about 25 mm.

In a further aspect of the connection member 13, an enlarged head 26 is provided. A shoulder 27 is situated between the head 26 and the machine threaded shank 25. While the shank 25 is sized to fit through an opening 22 in the upper plate 21 of the upper staple 12, the shoulder 27 has a diameter that is larger than the diameter of the opening 22. In this manner, the connection member 13 can apply a compressive force between the upper and lower staples as the threaded shank 25 is threaded into the boss 17. The shoulder 27 applies a force to the upper staple 12 to push it toward the lower staple 11.

In a further aspect of the invention, the head 26 of the connection member 13 is configured for engagement to an elongated member extending along the spine adjacent the instrumented vertebrae. In accordance with the invention, the head 26 can assume a variety of configurations provided that it can be firmly engaged to the elongated member. In the embodiment shown in FIGS. 1 and 2, the elongated member is a spinal rod, such as a spinal rod provided with the TSRH® Spinal System. In the specific embodiment illustrated in FIG. 1, the head 26 is generally U-shaped defining a slot 29 between posts 33 forming the U-shape. The head 26 can also define tool recesses 30 on opposite sides of the posts 33 so that the head can be gripped by a tool useful in threading the shank 25 into the threaded boss 17.

The head 26 further defines an engagement face 31 that is oriented toward the elongated member, or spinal rod. In a specific embodiment, the engagement face 31 includes a plurality of radial splines 32 emanating from the slot 29. In this illustrated embodiment, the head 26 of the connection member 13 is substantially identical to the head of the Variable Angle Bone Screw sold by Danek Medical, Inc. This bone screw is also depicted in U.S. Pat. No. 5,261,909, owned by the Assignee of the present invention. Specific reference is made to FIG. 2 of the '909 Patent and its accompanying description at column 4, lines 10–23, which figure and text are incorporated herein by reference. The '909 Patent further describes one manner in which the head of the variable angle bone screw is engaged to a spinal rod. Specifically, reference is made to FIGS. 3–5 and the text at column 4, line 35 through column 5, line 47, which description is incorporated herein. To summarize, the head 26 of the connection member 13, just like the head of the variable angle bone screw, is engaged to a spinal rod by way of an eyebolt and washer configuration. The washer includes splines that can mate with the splines 32 on the head 26. The washer also engages the spinal rod and permits connection of the head 26 to the spinal rod at variable angular orientations. Again, the details of this type of variable angle connection are now well known as shown in the '909 Patent.

While the correction device 10 is used for a closing osteotomy, the correction device 40, depicted in FIG. 2, is provided for use in an opening osteotomy. Like the correction device 10, the device 40 includes a lower staple 41 and an upper staple 42. The lower staple 41 includes prongs 45 configured for penetration into the cortical bone of a vertebra. A base plate 46 connects the prongs 45. Likewise, the upper staple 42 includes a pair of prongs 50 connected by an upper plate 51. Like the upper staple 12, the upper staple 42 also defines an opening 52 in the upper plate 51. The correction device 40 also utilizes the connection member 13 which is, in the specific embodiment, identical to the connection member 13 shown in FIG. 1. In that regard, the connection member 13 includes a shoulder 27 that prevents passage of the enlarged head 26 through the opening 52 in the upper plate 51 of the upper staple 42. The connection member 13 also includes an elongated machine threaded shank 25.

The connection device 40 further includes a wedge member 43 that is configured to be disposed within the osteotomy site to maintain the positioning of the portions of the vertebral body after the osteotomy is opened. Details of the lower staple 41 and the wedge member 43 that is engaged thereto, are shown in FIGS. 3–6. In one specific embodiment, the lower staple 41 includes a flat edge 47 and a curved edge 48. The wedge member 43 includes a wedge body 55 that is preferably fixed to the lower staple 41, such as by welding. The wedge body 55 defines a threaded bore 56 therethrough, that operates substantially similar to the threaded boss 17 of the lower staple 11 of the connection device 10 shown in FIG. 1. In particular, the threaded bore 56 can have a similar thread configuration to the threaded shank 25 of the connection member 13. A bore relief 57 is provided at the tapered end 61 of the wedge body 55. This bore relief 57 is preferably formed by angled faces converging toward the threaded bore 56. The relief 57 facilitates entry of the threaded shank 25 of the connection member 13 into the threaded bore 56.

The wedge body 55 further includes a flat end face 58 that is aligned with the flat edge 47 of the lower staple 41. On the opposite side of the wedge body 55 from the flat end face 58 is a curved face 60, which also corresponds to the curved edge 48 of the lower staple 41, both features being best shown in FIG. 5. The curved face 60 preferably conforms substantially to the anterior perimeter of the vertebral body. The flat end face 58 is provided for clearance from the spinal foramen in the vertebra. It is understood, that in some specific embodiments, the wedge member 43 can be symmetrically shaped—that is, the wedge body 55 can include a curved end face, such as end face 60, on both sides of the body.

Figure 6:
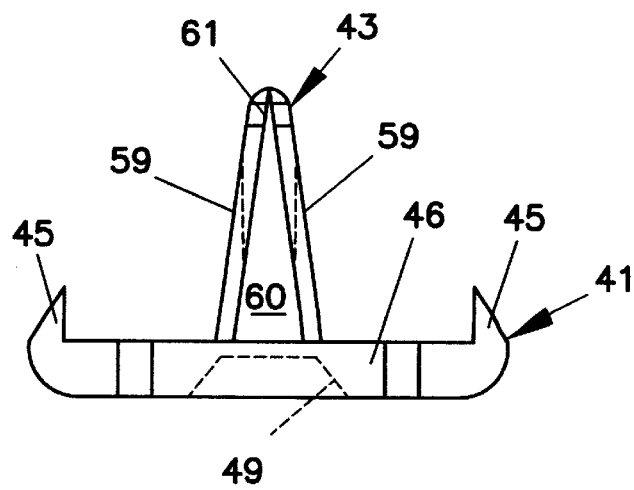
FIG. 6 is a side elevational view of the component shown in FIG. 3.

In accordance with certain aspects of the invention, it is important that the wedge body 55 provide as large an area as possible for contacting the portions of the vertebral body at the osteotomy site. This contact occurs at the angled side faces 59, which are best shown in FIGS. 3 and 6. The angled side faces 59 define an angle between each other that specifically corresponds to the amount of opening that is desired at the osteotomy site. In a specific embodiment, the angle between the angled side faces 59 is 15 degrees. In one specific embodiment, the wedge body 55 has a height of about 1.25 cm from the bore relief 57 to the lower staple 41.

In a specific embodiment, the lower staple 41 can have a relief bore 49 aligned with the threaded bore 56 of the wedge body 55. In this manner, the connection member 13 can have a length sufficient to partially extend into the relief bore 49 of the lower staple 41. Further in this specific embodiment, the edge of the angled faces, and more specifically the curved end face 60, is formed at a radius of 0.95 cm. Again, the dimensions of these features of the wedge member 43 can be modified depending upon the anatomy of the vertebra within which the wedge member is engaged. Moreover, if greater or lesser wedge angles are desired, the angle between the faces 59 can also be modified.

Figure 7A:
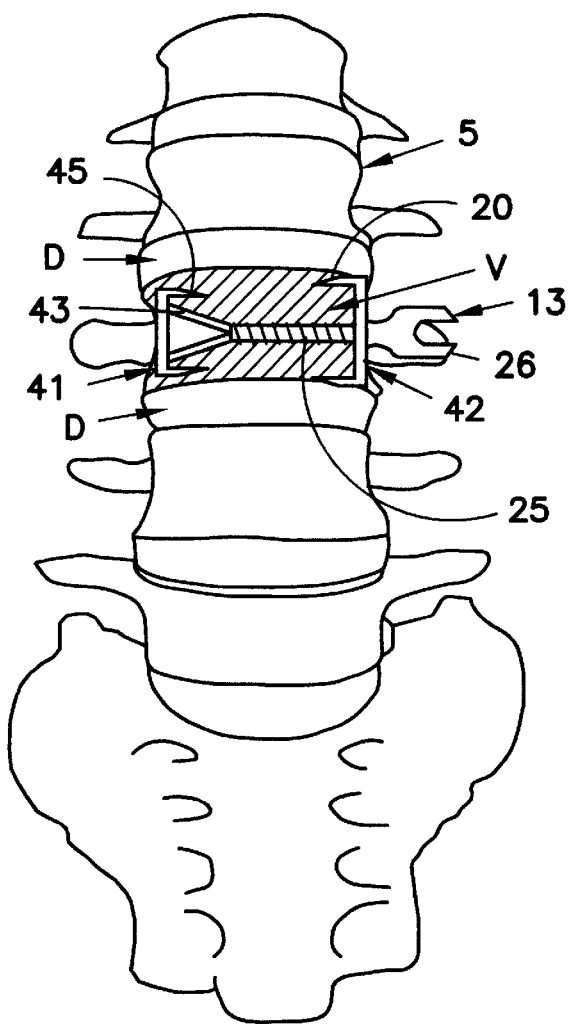
FIG. 7A is a view of the anterior aspect of a portion of the lumbar spine showing a correction device as depicted in FIG. 2 engaged within a vertebra.
Figure 8:
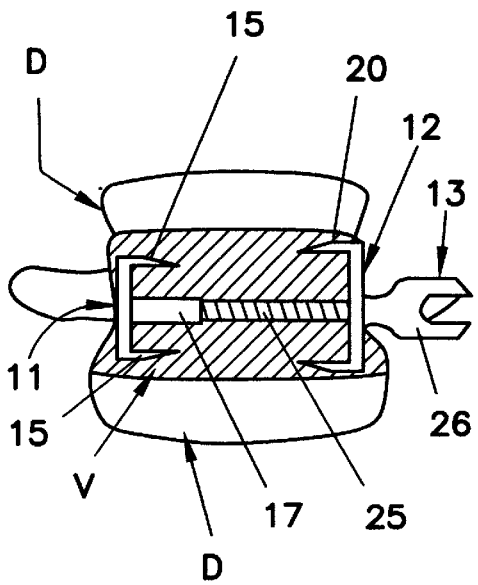
FIG. 8 is a view from the anterior aspect of the spine of a vertebral level with a correction device as depicted in FIG. 1 engaged within the vertebral body.
Figure 7B:
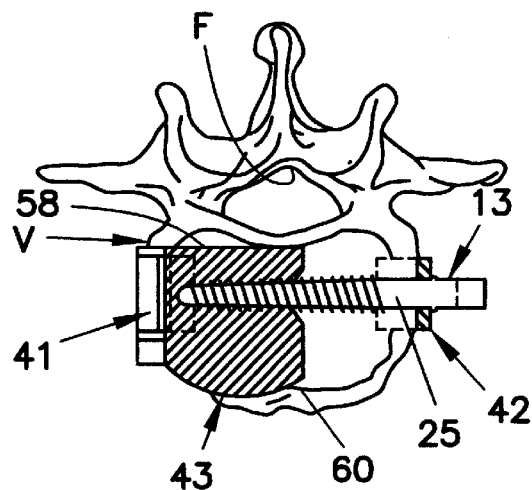
FIG. 7B is a view in the coronal plane of the instrumented vertebra in FIG. 7A with the correction device shown in cross-section.

One specific manner of placement of the correction devices 10 and 40 is shown in FIGS. 7A, 7B and 8. Looking first at FIG. 8, the correction device 10 is shown positioned in the anterior portion of the vertebral body. In particular, the connection member 13 spans essentially laterally across the vertebral body, with the lower staple 11 and upper staple 12 penetrating the cortical bone of the vertebral body. Preferably, the staples have a width sufficiently narrow to keep them out of the adjacent discs D and fully contained within the vertebral body V. In the specific embodiment of the connection member 13, the head 26 is oriented with its posts 33 aligned substantially within the coronal plane. In this manner, connection of the head 26 of the member 13 to a spinal rod by way of an eyebolt occurs with the spinal rod extending along the length of the spine.

Looking at FIGS. 7A and 7B, the correction device 40 is depicted engaged within a vertebral body V. Again, the correction device 40 extends transversely across the anterior portion of the vertebral body with the lower staple 41 and upper staple 42 penetrating the cortical bone. FIG. 7B illustrates the orientation of the wedge member 43 within the osteotomy site. It can be seen from this Figure that the curved face 60 approximates the anterior edge of the vertebral body V. The flat end face 58 then provides clearance for the vertebral foramen F so that the wedge member does not impinge upon the spinal cord within the foramen.

The connection devices 10 and 40 are preferably formed of a biocompatible sterilizable medical grade material. In some specific embodiments, the components of the correction devices 10 and 40 can be formed of stainless steel, while in other applications titanium can be the material of choice. In some embodiments, the wedge member 43 can be a solid member. In other embodiments, the wedge member 43 can be formed of a porous material, such as certain porous ceramics or a porous tantalum, such as HEDROCEL® produced by Implex Corporation. Alternatively, the wedge member 43 can include hollow portions with openings in the angled side faces 59 in contact with the vertebral body.

One object of these specific embodiments of the wedge member 43 is to permit tissue growth across and through the wedge member 43. One goal of the procedure of the present invention is to achieve bone union of the portions of the vertebral body at the osteotomy sites. In the case where the osteotomy is closed, bony material is in direct contact so that bone union can occur fairly easily and rapidly. On the other hand, introduction of the wedge member 43 into an open osteotomy site can delay this bone union. Providing a wedge member 43 that allows for tissue growth through and/or into the wedge member can enhance the likelihood and rate of bone union of an open osteotomy site. In a specific preferred embodiment, the wedge member 43 is preferably formed of the porous tantalum HEDROCEL® material which not only permits bone growth through the wedge member 43, but also allows the member to be fully integrated into the resulting bone union.

Figures 9, 10:
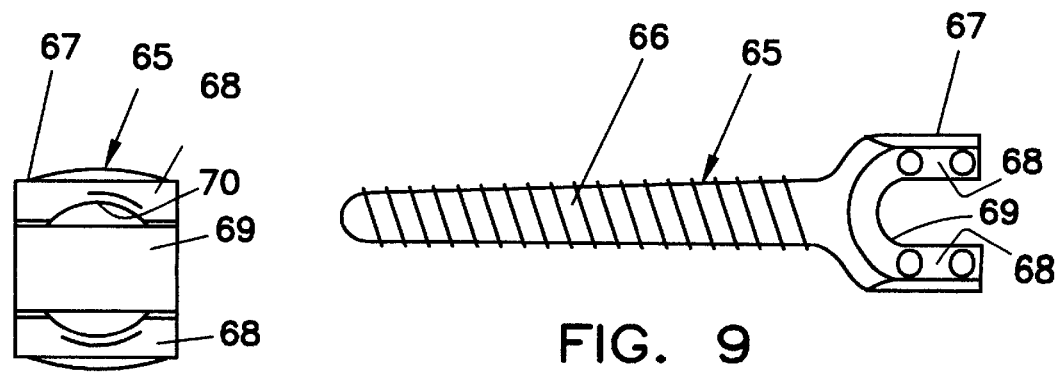
FIG. 9 is a side elevational view of an alternative embodiment of a connection element for use with the correction devices shown in FIGS. 1 and 2.
FIG. 10 is a top elevational view of the connection element shown in FIG. 9.

In an alternative embodiment, the connection member 13 for the correction devices 10 and 40 can be replaced by a connection member 65 as depicted in FIGS. 9 and 10. The connection member 65 includes a threaded shank 66 that can be identical to the threaded shank 25 of the connection member 13. The primary difference between connection member 65 and the prior member is that the head 67 of member 65 is configured to directly receive a spinal rod therein. Specifically, the head 67 includes a pair of opposite arms 68 which form a U-shaped rod channel 69 therebetween. The rod channel 69 has a width and diameter that is just slightly larger than the diameter of a spinal rod so that the rod can be seated within the channel. The arms 68 further define an internally threaded bore 70 that intersects the rod channel 69. A threaded plug (not shown) can be used to clamp the rod within the rod channel by threading into the threaded bore 70. The head 67 of the connection member 65 of the present embodiment can be similar to the head of certain bone screws provided with the CD®, CCD® and CD Horizon® Spinal Systems sold by Sofamor, S.N.C., a subsidiary of Sofamor Danek Group. Some details of the construct can also be found in U.S. Pat. No. 5,147,360, assigned to Sofamor, S.N.C. Particularly, FIG. 5 of the '360 Patent, together with the specification at column 4, lines 44–55, which disclosure is incorporated herein by reference, show one embodiment of a head of a bone screw for use with the present invention.

In the preferred embodiment, connection member 65 is preferred since it permits top loading introduction of the rod into the head of the member when the correction devices 10, 40 are implanted within the patient. It is understood that different head configurations for the connection members can be provided depending upon the type of elongated member extending along the length of the spine and the type of connection desired. For example, if the elongated member extending along the length of the spine is a plate, the head, such as head 26 of connection member 13, can be in the form of a machine threaded post. This machine threaded post could then be engaged through a slot in the elongated plate by way of a nut. Such a connection is accomplished in the DYNALOK® bone bolt and plate sold by Danek Medical, Inc. Details of such a connection can also be found in U.S. Pat. No. 5,545,163, assigned to Danek Medical, Inc., and particularly in FIGS. 6 and 10 and their accompanying descriptive text, which is incorporated herein by reference. Alternatively, the head of the connection member can be closed, meaning that the elongated member spanning the length of the spine must be threaded through an opening defined in the head of the connection member. Regardless of the manner in which the connection member is engaged to a particular elongated member spanning the spine, in order to achieve one object of the invention, the elongated member should be capable of removal once bone union occurs at the osteotomy sites.

An example of using the correction devices 10 and 40 of the present invention, along with the inventive surgical techniques, can be understood with reference to FIGS. 11–14C. Referring first to FIG. 11, a portion of a patient's spine from $T_3$ to the sacrum is shown in which the spine has a scoliotic curve. As can be seen in the Figure, the apex of the curve is offset a distance D from its correct alignment in the coronal plane. In other words, the spine is deformed laterally so that the axes of the vertebral bodies are displaced from the sagittal plane passing through the spine of the patient. It should be understood that the spinal deformity depicted in FIG. 11 is but one of many types of spinal deformities that can be addressed by the devices and techniques of the present invention. Most commonly the devices and techniques are expected to be used for either primary thoracic or thoracolumbar curves. They can be used for correction of the thoracic curve as an isolated curve, or the lumbar curve as an isolated curve.

In correcting the curved deformity shown in FIG. 11, wedge osteotomies $R_6$–$R_{11}$ can be cut from the thoracic vertebra $T_6$–$T_{11}$ at the convex side of the curvature. Preferably, a 15 degree osteotomy wedge of bone from the vertebral body is removed, although other wedge dimensions can be accommodated depending upon the amount of curvature and lateral offset of the particular vertebra. In the lumbar spine, opening osteotomies $X_1$–$X_4$ are shown cut into the vertebra $L_1$–$L_4$. They could be cut into $T_{11}$ to $L_4$. In the lumbar spine for this particular curvature, no bone material is removed. Instead, the vertebral body is essentially fractured to permit an opening osteotomy at that vertebral level. Again, the cut into the lumbar vertebrae occurs on the same side of the spine as the wedge osteotomies in the thoracic vertebrae. The various osteotomies in the thoracic and lumbar vertebrae can be performed using conventional tools and instruments, such as a chisel and an osteotomy spreader.

Once the osteotomy sites have been prepared in each of the affected vertebrae, the spine can be manipulated to close the closing osteotomies $R_6$–$R_{11}$ and open the lumbar osteotomies $X_1$–$X_4$. The spine would then appear as shown in FIG. 12 in which the thoracic osteotomies are closed at sites $C_6$–$C_{11}$ and the lumbar osteotomy sites are left open at sites $W_1$–$W_4$. In the configuration shown in FIG. 12, the lateral offset of scoliotic curvature is reduced to an offset D' that is significantly less than the original curvature deformity. Ideally, the offset D' would be negligible so that the spine would appear properly aligned in the coronal plane.

The determination of the location and nature of the opening and closing osteotomies can be determined after a review of A-P and lateral radiographs of the spinal deformity. In some senses, the identification of the osteotomies is a matter of geometry. For example, in the thoracic spine, each closing osteotomy will eliminate a certain amount of the abnormal curvature as the osteotomy is closed as shown in FIG. 12. Similarly, each opening osteotomy in the lumbar spine will cause an effective translation of the particular lumbar vertebra toward the spinal midline. The amount of effective shifting of the axis of a lumbar vertebra toward the spinal midline can be based upon the size of the opening wedge osteotomy performed at that vertebra. It is, however, preferable that the opening or closing wedge osteotomies not exceed a 15 degree segment removed from or added to the vertebral body, in order to preserve the vertebral architecture as much as possible and to reduce the possibility of narrowing of the disc space.

Once the thoracic osteotomies are closed and the lumbar osteotomies are opened, the correction devices 10 and 40 can be engaged to the respective vertebrae. For example, the correction device 10 is engaged to the thoracic vertebrae, with the lower staples 11 positioned on one side of the vertebral body, and upper staples 12 positioned on the contra-lateral side of the vertebral body. The connection member, which can be member 65 in FIG. 9, is then engaged between the upper and lower staples. In preparation for engagement of the connection member 65, a bore can be formed laterally through the vertebral body essentially through the centerline of the osteotomy. In certain techniques, the centerline of the osteotomy will extend laterally through the vertebral body and generally intersecting the center of the body. The bore can be prepared using a conventional drill or even using a curette.

A similar procedure is performed to introduce the correction device 40 to the lumbar vertebrae. In this instance, the wedge members 43 are disposed within the open osteotomy sites $W_1$–$W_4$. The lower and upper staples 41, 42, respectively, are then engaged to the vertebral bodies. The staples of both correction devices 10 and 40 are used to press the halves of the vertebral body together to close the osteotomy site as in the thoracic vertebrae, or to press the vertebral halves against the wedge member 43. Prior to closing each of the osteotomies, bone fusion material or bone cement can be introduced into the osteotomy site to facilitate complete closure and ultimate bone union.

Once the correction devices 10 and 40 are engaged to their particular vertebrae, the elongated member, such as spinal rod 72, can be engaged to each of the connection members 65 in the manner described above. Depending upon the configuration of the spine after performance of the osteotomies, the spinal rod 72 may be pre-bent to a particular curvature. In the configuration shown in FIG. 13, a certain amount of lateral curvature remains so that the rod would be pre-bent to emulate that lateral curvature. Further straightening of the spine can be accomplished if the rod 72 does not completely emulate the intermediate corrected curvature. In that instance, some widening and narrowing of the intervertebral disc space may occur, but it may be expected that the disc space height would be restored once the spinal rod 72 is removed.

Figure 13:
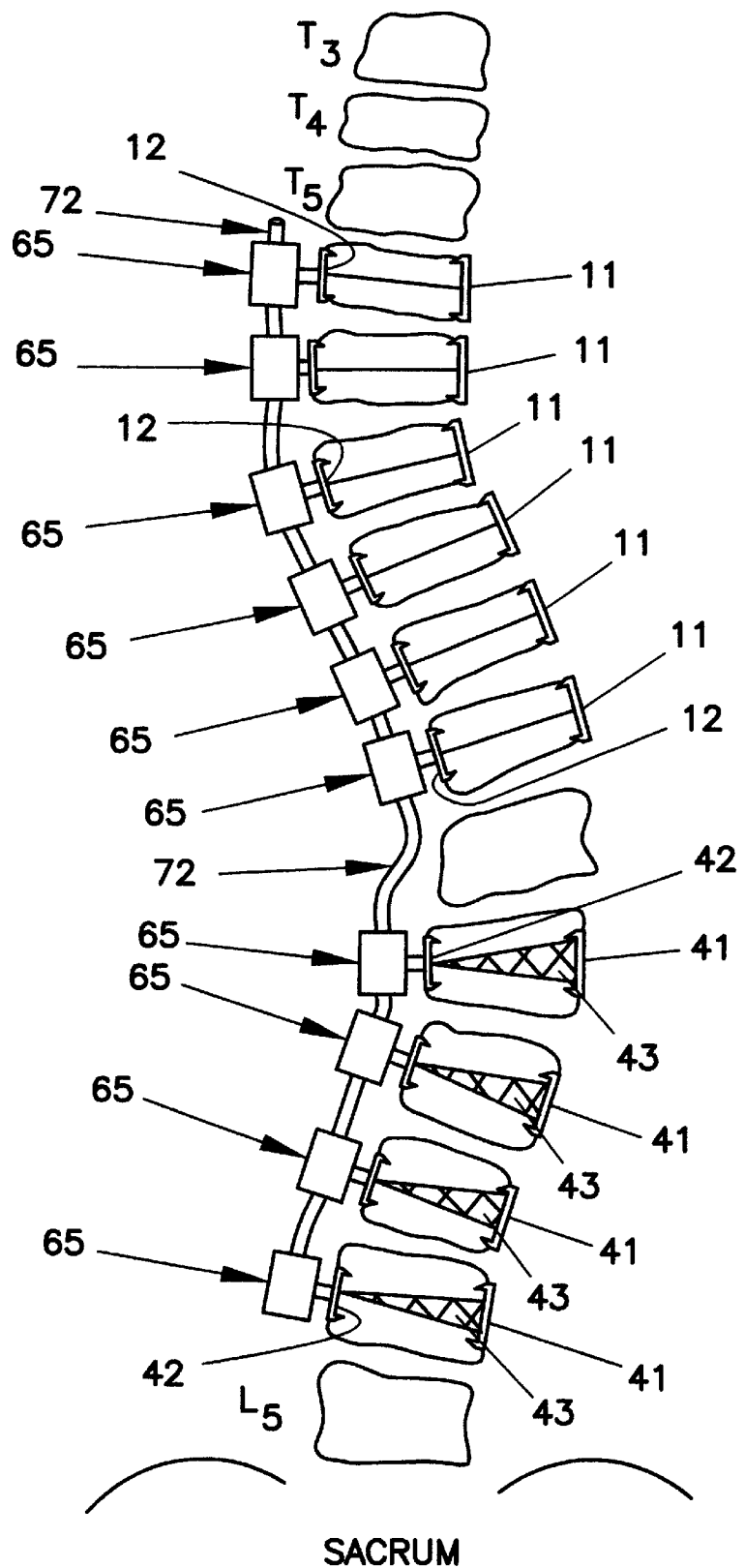
FIG. 13 is a view of the corrected spine shown in FIG. 12 with the inventive instrumentation engaged to the instrumented vertebral levels.
Figure 15:
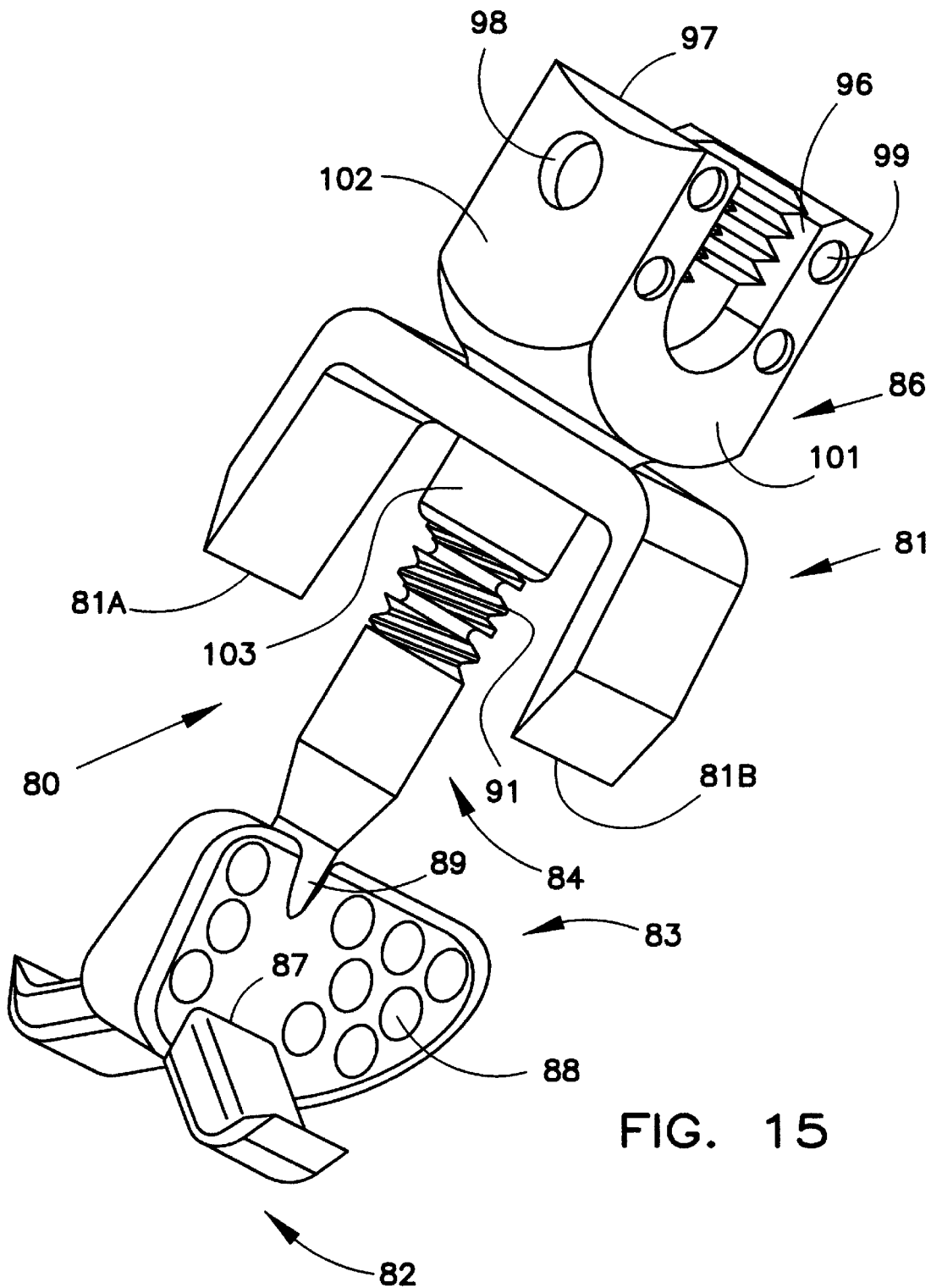
FIG. 15 is a perspective view of a correction device according to the present invention and with further improvements.
Figure 16:
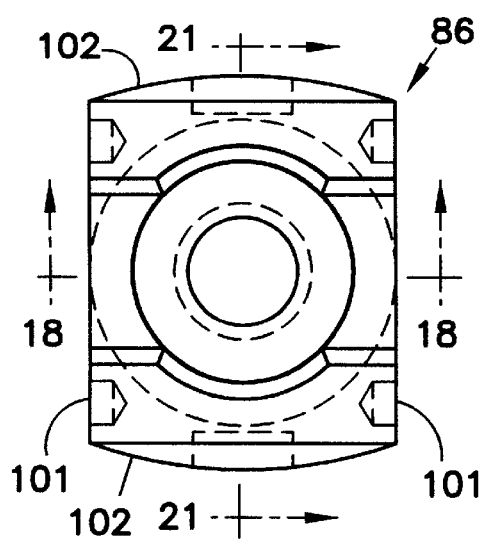
FIG. 16 is a top plan view of a spinal rod receiving head of the correction device of FIG. 15.

In addition to any residual lateral curvature following the implantation of the correction devices, the spinal rod 72 is preferably bent to correspond to the normal kyphotic and lordotic curvatures of the thoracic and lumbar spine segments. In this manner, the flat back syndrome can be avoided. Care must be taken that the sagittal plane curvature of the spinal rod 72 not exceed the physiologic capability of the spinal segments. In other words, the deformed spine of a patient may also have a curvature deformity in the sagittal as well as the coronal planes. Under some circumstances, the rod rolling technique frequently utilized with the CD® Spinal System can also be implemented where an intermediate corrected residual curvature remains. In that instance, pre-bending the rod 72 to conform to that residual curvature, such as shown in FIG. 13, can also approximate the normal kyphotic and lordotic curvatures for a healthy spine. Thus, it can be contemplated that the rod 72 shown in FIG. 13 can be rolled about its axis so that the spine becomes perfectly aligned in the coronal plane with the restoration of the normal curvature in the sagittal plane. Also, separate rods and different rod locations may be used for addressing thoracic spine problems separate from lumbar spine problems.

In accordance with a preferred technique of the present invention, the correction devices 10 and 40 and the spinal rod 72 are implanted from an anterior approach. In contrast to prior techniques for the correction of scoliosis, only a single rod is required to maintain the stability of the correction. Since the physiology of the discs and vertebrae are not being changed, the elastic strength of the intervertebral discs will help retain the spinal column in its corrected configuration. Where each of the vertebral bodies is held together by way of staples on opposite sides of the body, there is substantially no risk that the osteotomy sites will separate or fail. Thus, it can be seen that the present invention takes advantage of the natural strength of the spine in order to retain the stability of the temporary fixation at least until bone union occurs. Depending upon the overall health of the patient and of the vertebral bodies, this bone union can occur in a manner of a few months.

Once bone union has occurred and the vertebral bodies are essentially healed, the spinal rod 72 is no longer essential to maintain the stability of the spine. In this case, the rod 72 can be removed by disconnecting it from each of the connection members 13 or 65, leaving only the head of the connection member projecting beyond the vertebral body. At this point, the intervertebral discs resume their normal function and the patient's spinal column is as close to a normal configuration as possible. While the preferred embodiment of the invention envisions completely removing the spinal rod and associated connectors, such as eyebolts and machine threaded nuts, a biodegradable or resorbable rod can also be contemplated. In this instance, the rod would gradually resorb. Similarly, the correction devices 10 and 40 also become superfluous once bone union is achieved at the osteotomy site. Thus, the components of the correction devices can also be resorbable. One example previously discussed is the formation of the wedge member 43 out of a porous tantalum or HEDROCEL® material. A similar material may be usable to form the staples and the connection members, provided that the material forming these components can still meet their strength requirements.

In certain applications of the devices of the present invention, the spinal rod or elongated member may not be necessary to stabilize the instrumentation. For instance, if only a few vertebrae are instrumented with a correction device, the elongated spinal member or rod may not be required. Since the present invention contemplates correction of spinal deformities without fusion, additional fixation devices are not as essential as in other procedures in which fusion occurs. In those other procedures, the spinal segments must be essentially immobilized in order for the bony bridge to be formed across the intervertebral disc space. These same requirements are absent in the present inventive technique using the novel devices described above. In the instance in which a spinal rod is eliminated, it is of greater importance that the upper and lower staples hold their position within the vertebral body to thereby hold the osteotomy sites in their preferred orientation. Thus, the connection members 13, 65 as previously described, provide a compressive force between the upper and lower staples to hold them within the vertebral body. It is understood, that this compressive force is not so great as to cause subsidence of the staples within the vertebral body. In cases in which the spinal rod 72 is not utilized, the connection member 13, 65 does not require the presence of a head 26, 67 which would ordinarily be engaged to the spinal rod. Instead, the connection member can be modified to simply include an enlarged shoulder 27 with a driving tool recess formed in the shoulder to receive a driving tool for threading the threaded shank 25, 66 of the connection member into the threaded boss 17 or the threaded bore 56. In the cases in which the spinal rod is eliminated, the vertebrae will be held in their corrected position by the elasticity of the intervertebral discs. Since the geometry of the vertebral bodies has been altered, the spine should automatically assume its corrected position, even without the assistance of an additional member spanning the spine.

The present invention also contemplates a surgical technique in which curvature deformities in multiple planes can be corrected. For instance, in many cases, the patient's spine suffers not only from scoliosis, but also from some degree of kyphosis or lordosis. In this instance, correction of an abnormal curvature must occur in two planes. The present invention readily permits such a correction.

Figure 14A:
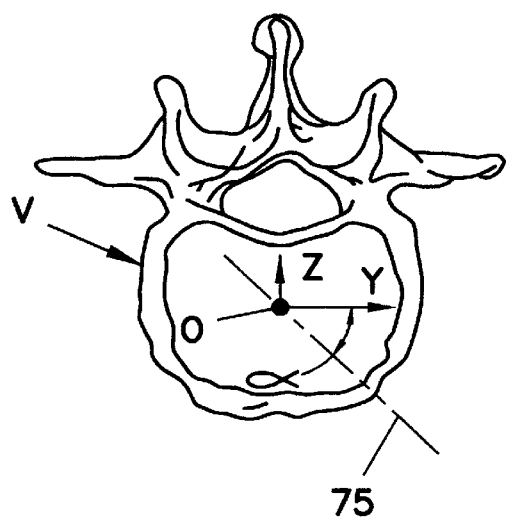
FIG. 14A is a view of a vertebra in the coronal plane showing an axis for performing an osteotomy in conjunction with a method of the present invention.
Figure 14C:
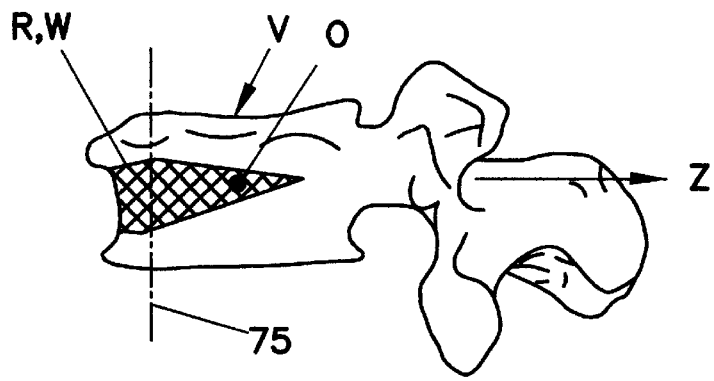
FIG. 14C is a lateral view of the vertebra in FIG. 14A in which the osteotomy site is shown in cross-hatch.
Figure 14B:
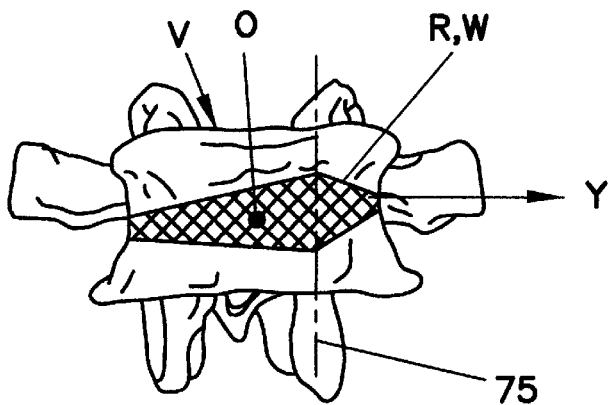
FIG. 14B is an anterior to posterior view of the vertebra in FIG. 14A in which the osteotomy site is shown in cross-hatch.

As shown in FIG. 14A, the vertebral body V has an axis Z from the center of the vertebral body directed posteriorly and an axis Y directed laterally within the coronal plane. In cases where the particular vertebral body is misaligned in two planes, the centerline of the osteotomy 75 can be oriented at an angle α relative to the axis Y. In the procedures previously described, the centerline 75 of the osteotomy corresponds or is aligned with the axis Y. As can be seen in FIGS. 14B and 14C, removal of bone material for a closing osteotomy R, or addition of a wedge member for an opening osteotomy W is depicted. The angular orientation of the osteotomy at the angle α achieves correction and re-alignment of the vertebra in two planes.

Referring now to FIGS. 15–18, the correction device 80 is shown therein, is similar in many respects to that of FIG. 2. For example, it includes a bone-piercing device 81 in the form of a staple very similar to the staple 42 in FIG. 2. It also includes a bone-piercing device 82 at the opposite end and also in the form of a staple, although considerably modified in shape to better fit the surface of the intervertebral body as best shown in FIG. 19A, thereby matching the profile of the concave portion of the vertebral body. It also includes a wedge 83, a screw 84, and a head 86. There are some differences which will be described now.

Figure 18:
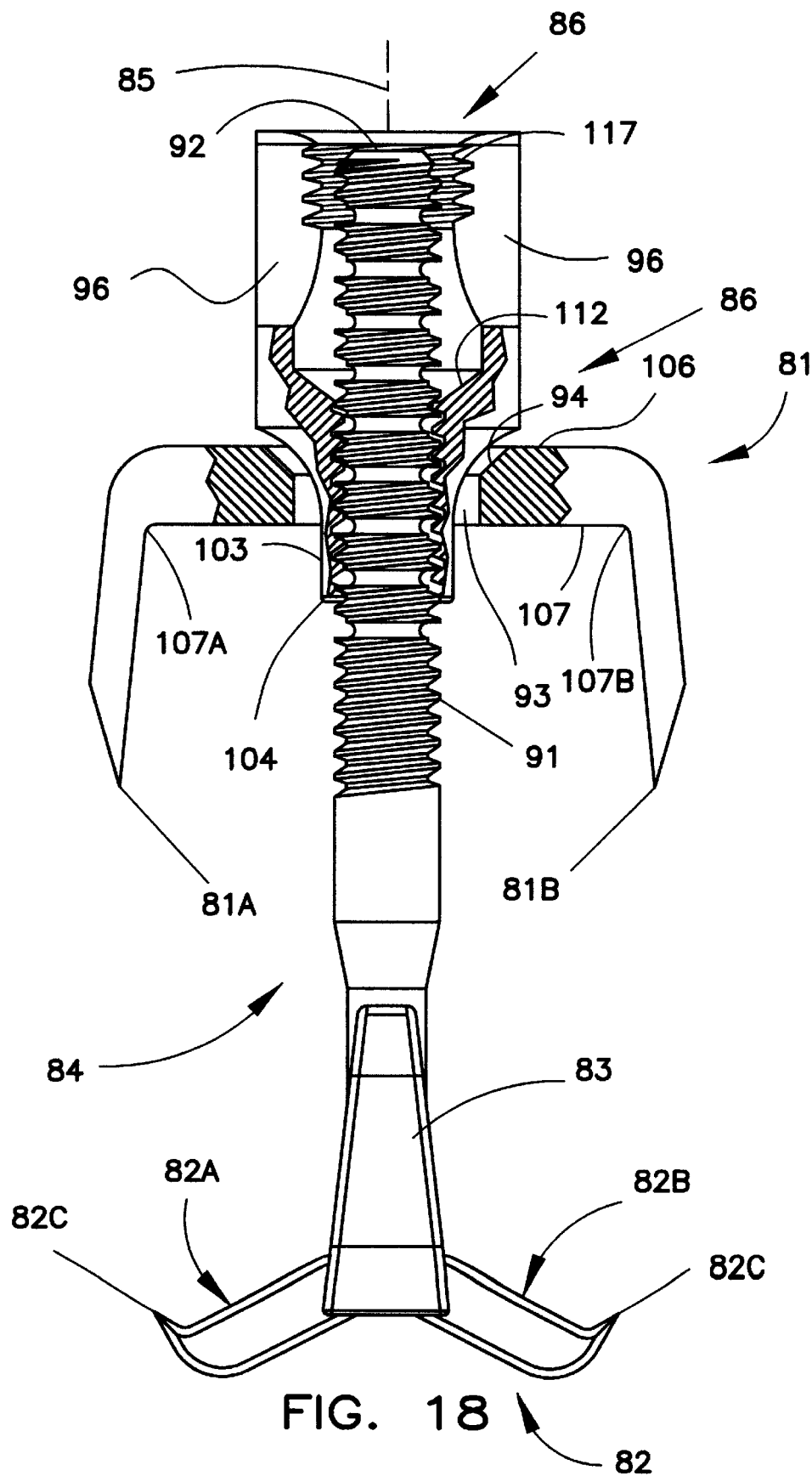
FIG. 18 is a partial sectional view of the device taken at line 18—18 in FIG. 17 and viewed in the direction of the arrows.
Figure 19A:
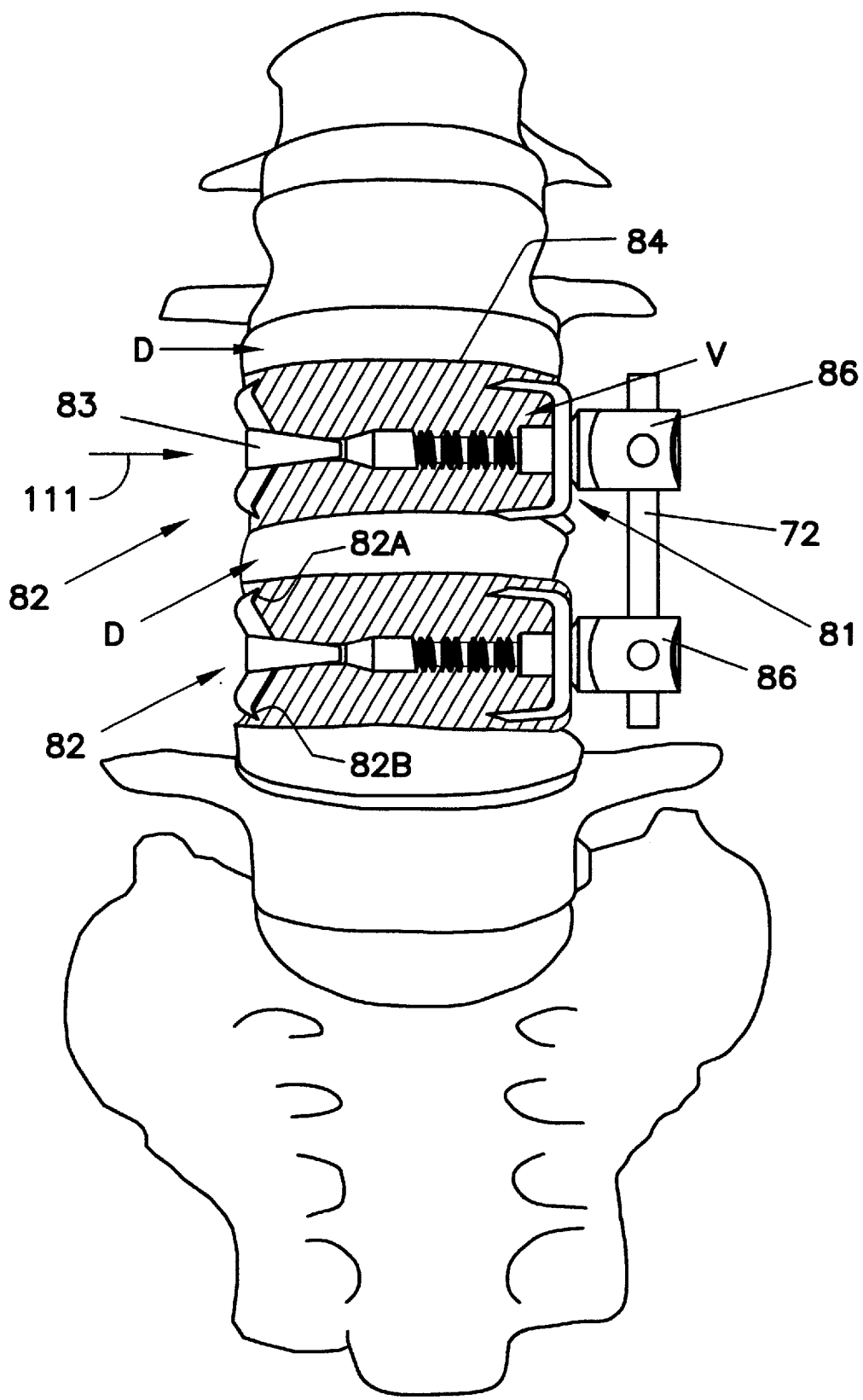
FIG. 19A is a view of the anterior aspect of a portion of the lumbar spine showing two of the correction devices of FIG. 15 engaged in adjacent vertebral bodies with a spinal rod fastened to them and shown fragmentarily.

Viewed as shown in FIG. 18, the staple 82 described briefly above has a shape suggesting an inverted gull-wing or a wide "W". The wedge 83 is fixed to the staple 82 by welding, press fit or any other suitable means at 87. The wedge has a plurality of apertures 88 through it which serve to reduce mass and encourage bone growth through the wedge. The screw 84 is fixed to the wedge at 89 and/or staple 82 by welding, press fitting or otherwise.

Figure 19B:
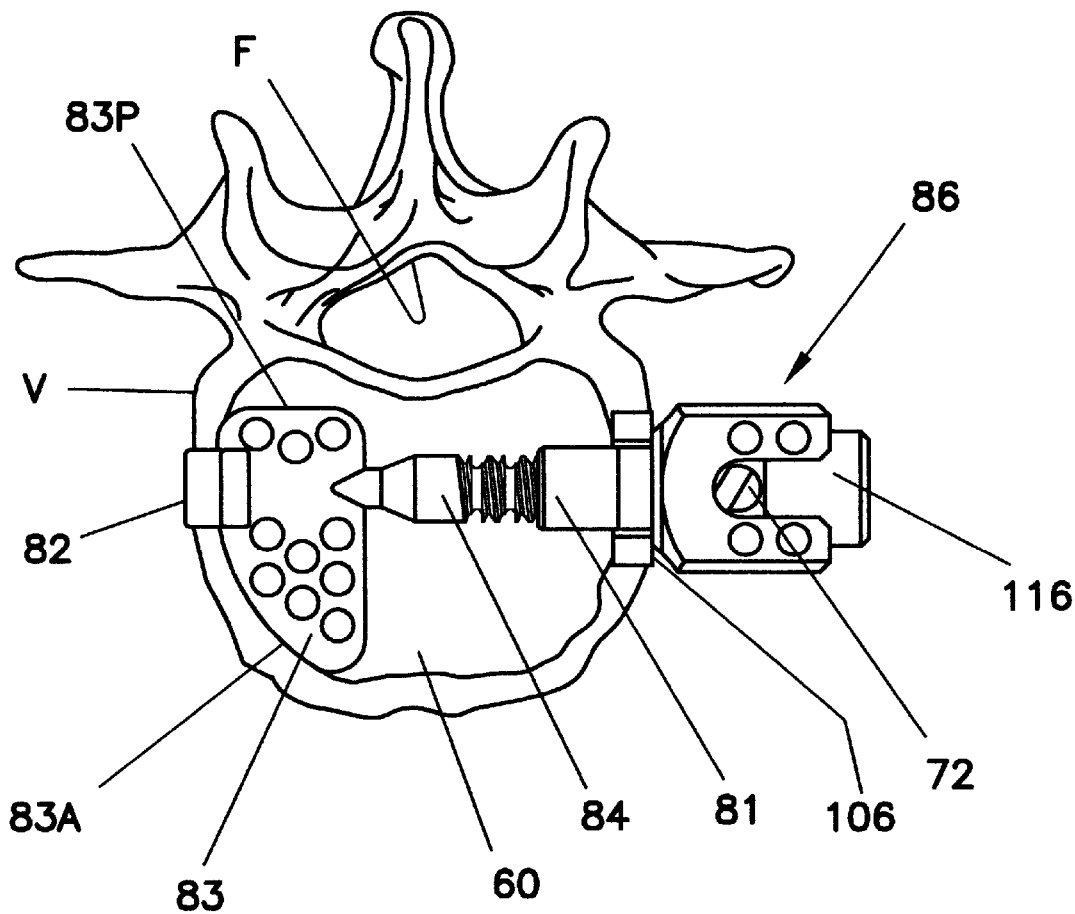
FIG. 19B is a view of the correction device of FIG. 15 installed as in FIG. 19A and viewed in the coronal plane.
Figure 20:
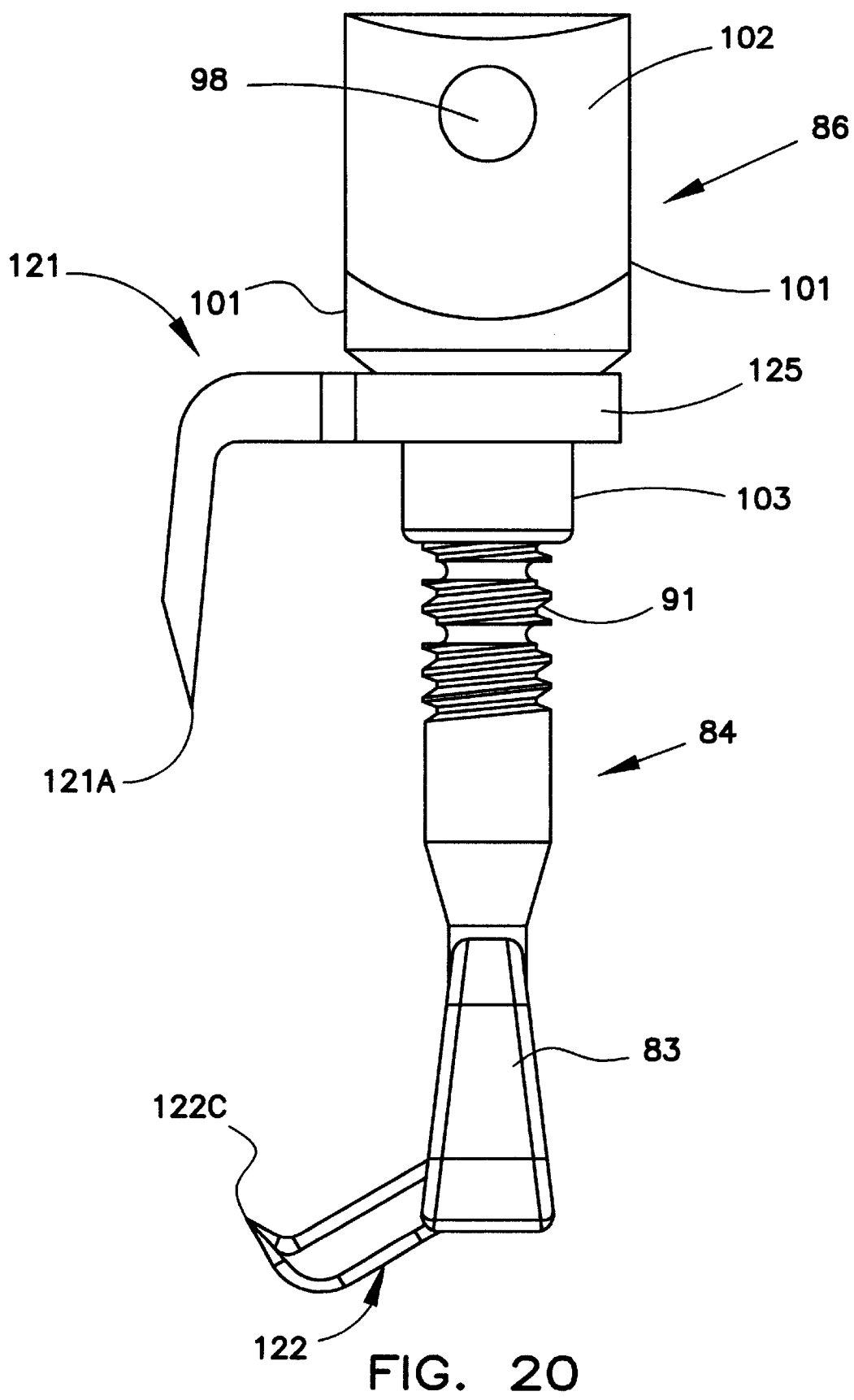
FIG. 20 is an elevational view of another embodiment of the correction device.
Figure 21:
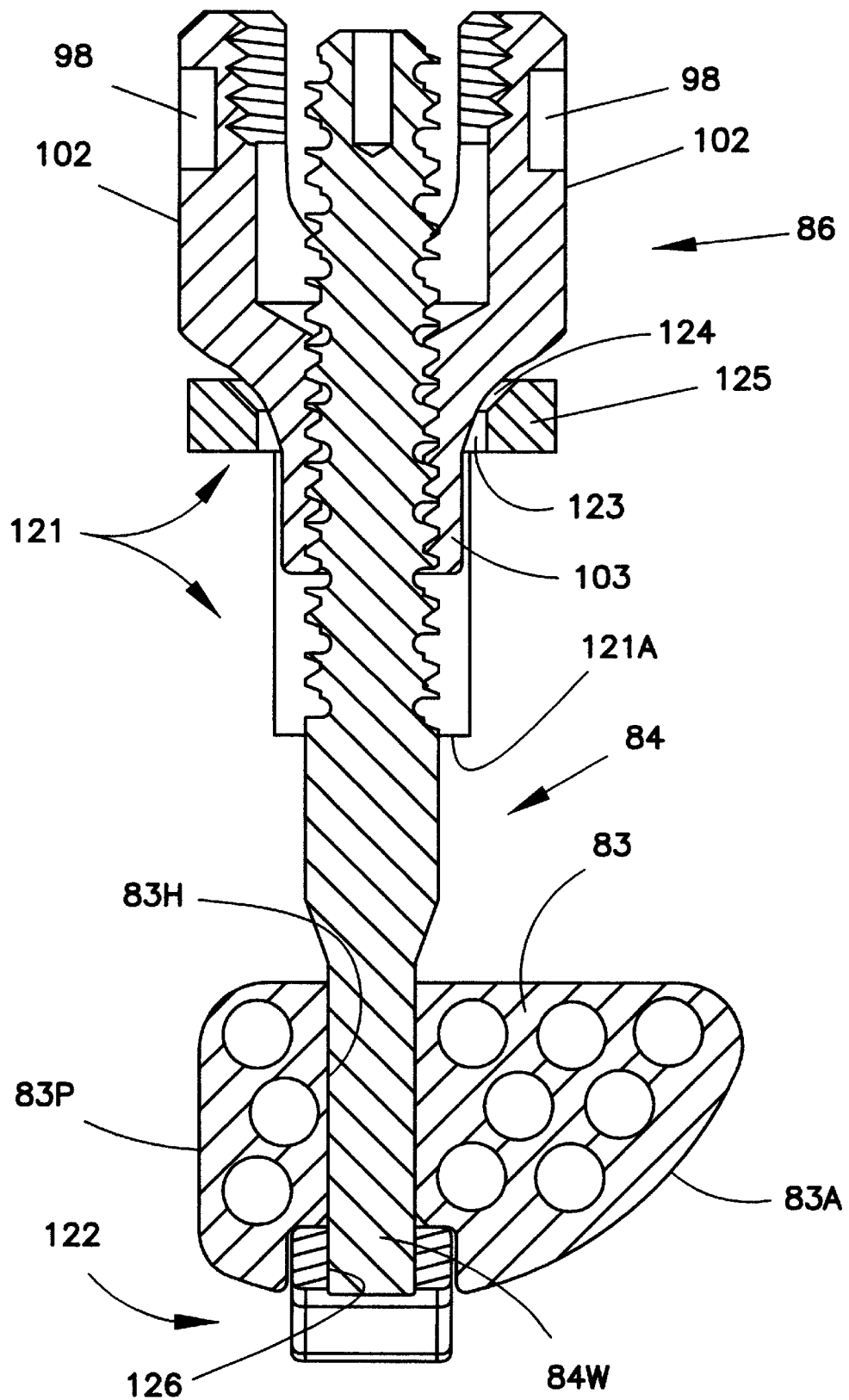
FIG. 21 is a section through the device of the FIG. 20 embodiment taken at line 21—21 in FIG. 16 and viewed in the direction of the arrows.

The head 86 has internal threads which are threaded onto the external threads 91 extending from the outer end 92 of the screw. The head-end bone-piercing anchoring device 81 has a central aperture 93 through it, with a chamfer 94 at the top. The head has the outwardly opening U-shaped channel 96 opening at the outer end 97 thereof to receive a spinal rod such as 72 (FIGS. 13, 19A, 19B). There are also the usual tool receiver opening such as 98 and 99 that are usually provided for this type of head which has been in use by the assignee of the subject application and marketed under the assignee's CD Horizon® brand. The head may be of other shapes for other styles of devices for intervertebral attachment.

Further referring to head 86, the oppositely facing flat outer surfaces 101, and curved outer surfaces 102 blend into a base 103 having the concave surface blending from those faces into the base toward the inner end 104 of the base. This concave surface can successfully seat at the outer face 106 (FIG. 18) of the bone-piercing anchor device 81 without the surface 106 being in a plane perpendicular to the screw axis 85. In this way, good anchorage in the vertebral body can be achieved even if one or the other of the two prongs of the piercing device 81 does not fully penetrate the vertebral body. Also it enables the outer portions 107A and 107B of surface 107 to contact the vertebral body, even if the axis of aperture 93 is not colinear with axis 85 of the screw. Here it should be mentioned that the head-end anchor 81 can be shaped such that, as viewed in the direction represented in FIG. 18, it would suggest a wide "M" or a gull wing appearance like that of anchor 82, but not inverted. This could be used to conform the shape of the head-end anchor more closely to the profile of the vertebral body, if desired.

In the use of the FIGS. 15–18 embodiment of the invention, the procedure described above with reference to the lumbar spine in FIG. 11, can be followed. After performing the opening osteotomy and providing a hole through the vertebral body, the threaded end of the screw is inserted from one side of the vertebral body in the direction of arrow 111 in FIG. 19A. Then, with the bone piercing anchor 81 installed loosely on the base 103 of the head 86, the head is screwed onto the threads 91 of the screw 84, with the first and second anchors 82 and 81 oriented as shown in FIG. 19A. These devices are maintained in this attitude as the head is advanced on the screw threads until both the sharp edges of the prongs of the anchors are thoroughly seated in the vertebral body. Then the screw threads extending outward beyond the countersink 112 (FIG. 18) in the head, can be clipped or broken off with tooling already known in the art for performing that step with the CD Horizon® instrumentation or other instrumentation known in the art. Bone fusion material or bone cement can be introduced into the holes 88 in wedge 83 prior to insertion of the screw, if desired, to enhance the function of whatever bone fusion material or bone cement may have already been introduced into the osteotomy site prior to installation of the screw.

After the desired correction devices have been installed in the vertebral bodies in the manner described above, the rod 72 as previously described, is installed in the slots 96 and clamped in place by the set screw 116 threaded into the threads 117 of the head 86 in FIG. 19B. As shown in FIG. 19A, the inwardly facing surfaces 82A and 82B generally conform to the curvature of the concave side of the vertebral body. The bone-piercing edges 82C of the device 82, and which, when combined with the surfaces 82A and 82B present in FIG. 18 the appearance of "bird beaks", are thereupon securely anchored in the vertebral body. Also, it should be noted in FIG. 18, that the sharp end 81A and 81B of the bone-piercing prongs of the member 81 are spaced at a slightly greater distance than at the bends 107A and 107B, providing a slight inward taper to assist this member 81 in anchoring in the bone and holding the bone snug against the angled side faces of the wedge.

Figure 22:
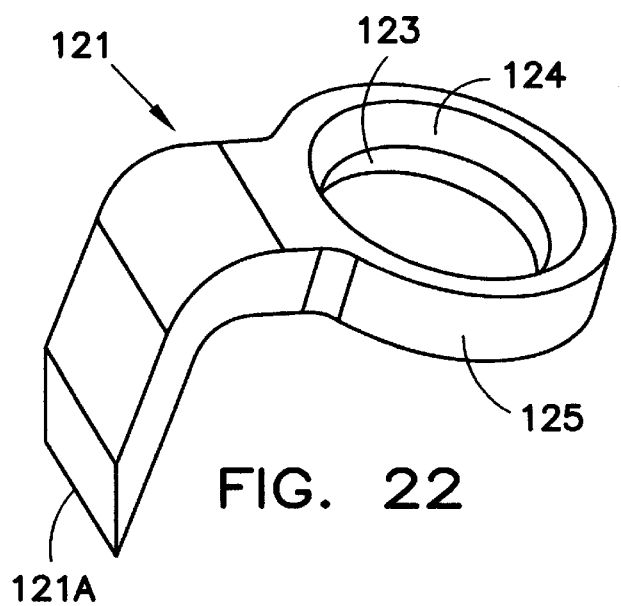
FIG. 22 is a perspective view of the outer or top bone anchoring device of the FIG. 20 embodiment.
Figure 24:
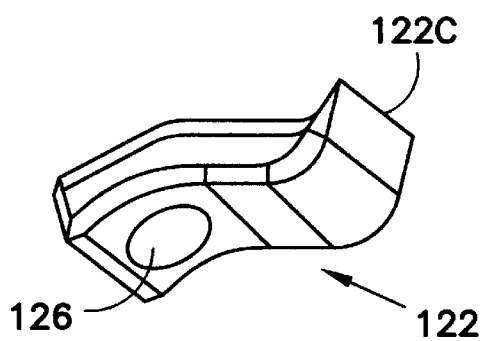
FIG. 24 is a perspective view of the bottom or inner end bone anchoring device according to the FIG. 20 embodiment.
Figure 23:
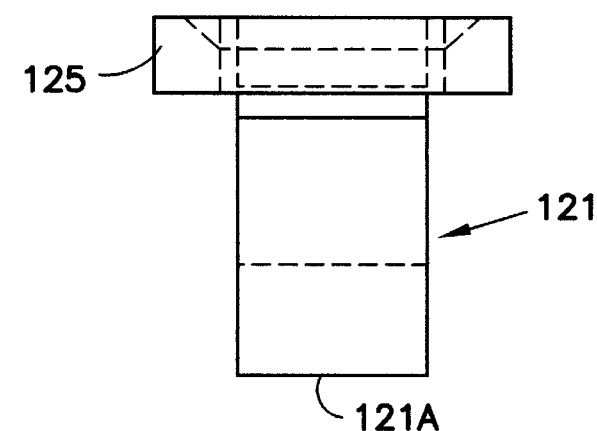
FIG. 23 is an elevational view thereof.
Figure 25:
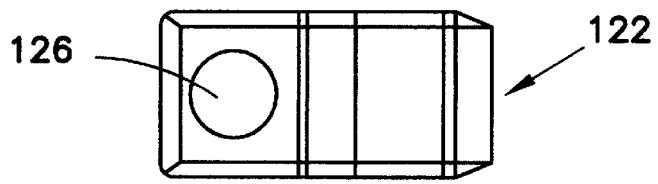
FIG. 25 is a plan view of the device of FIG. 24.
Figure 17:
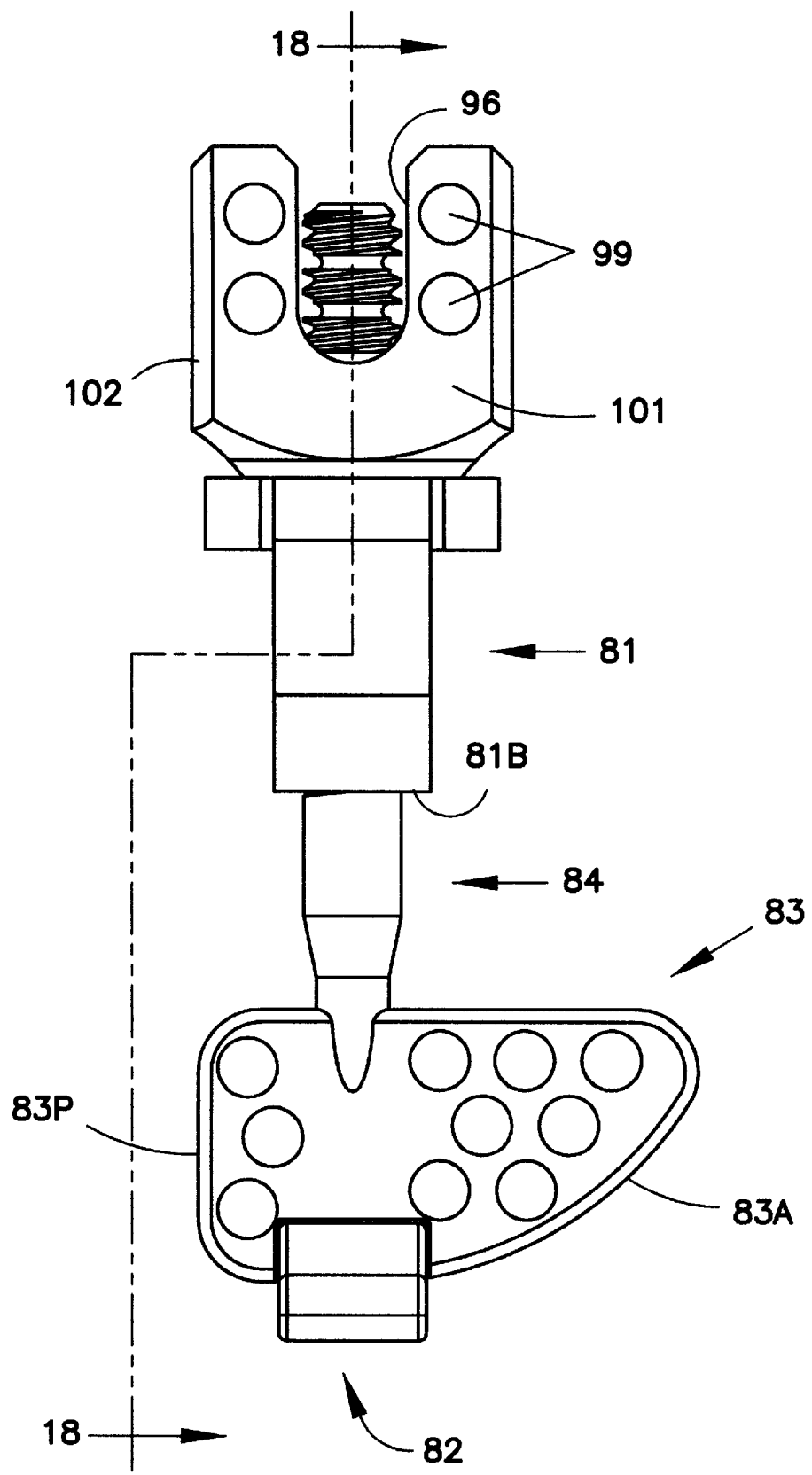
FIG. 17 is an elevational view of the correction device of FIG. 15.
Figure 26:
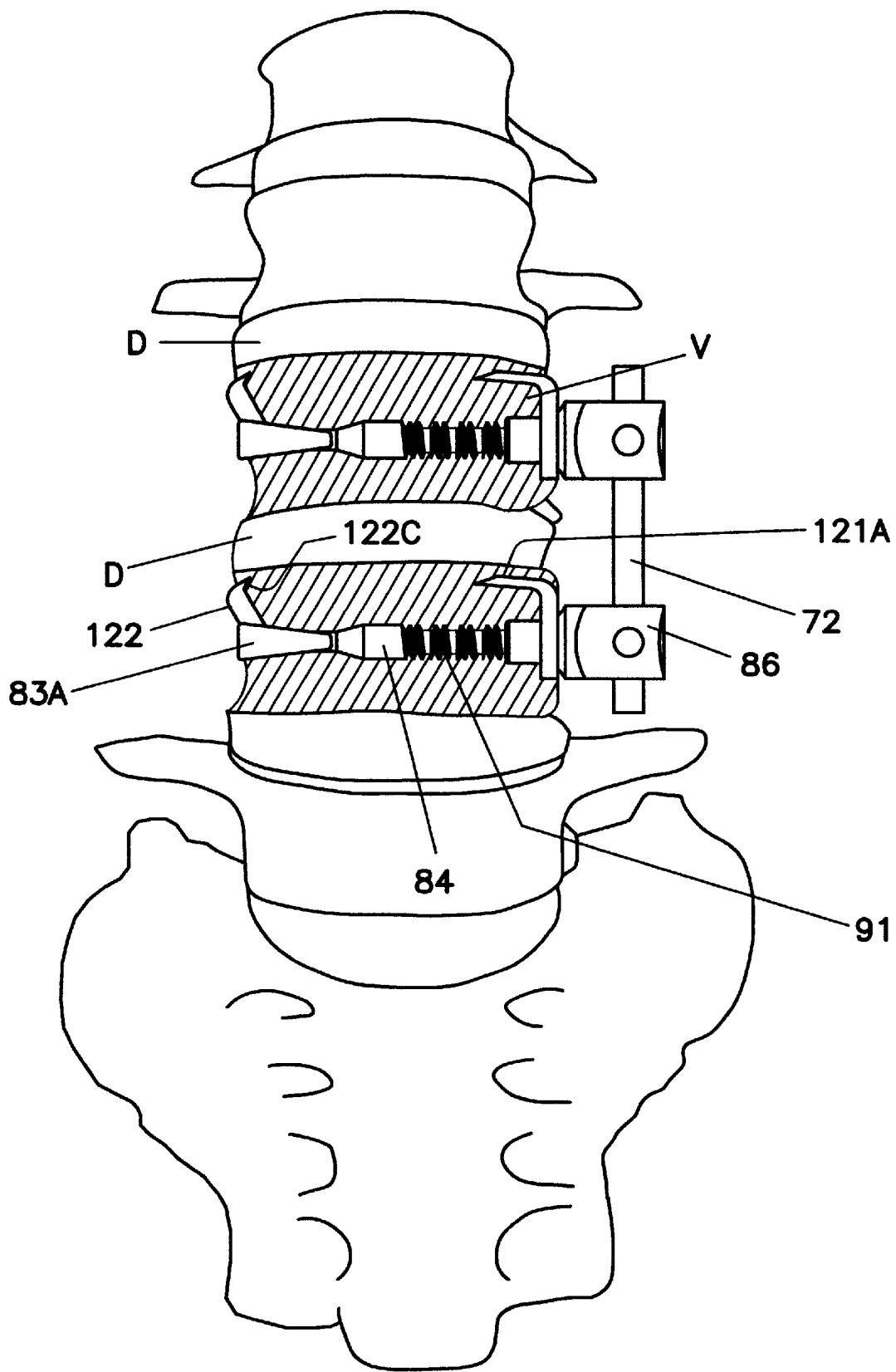
FIG. 26 is a view similar to FIG. 7A and 19A but illustrating application of the embodiment of FIG. 20.

Referring now to the embodiment in FIGS. 20 through 25, all of the features of this embodiment are the same as those in the embodiment of FIGS. 15–19B except for elimination of one of the prongs of each of the head-end bone-piercing device 121 and the wedge-end bone-piercing device 122. The installation is much the same as described above for the embodiment of FIGS. 15–19B and shown in FIGS. 19A and 19B. As shown in FIG. 26, the preference is to have the bone-piercing device at each of the head end and wedge end of the assembly above the screw axis and the screw axis slightly below the coronal mid-plane of the vertebral body. As shown in FIG. 22, the upper bone-piercing member has a sharpened straight edge 121A, like 81A of the FIG. 15 embodiment and the central opening 123 with the upper edge chamfer 124 in the ring portion 125 of this device. The wedge end of bone-piercing device 122 has an aperture 126 through it which receives the wedge end 84W of screw 84 which, as mentioned above, is identical to that in the FIG. 15 embodiment. Also as indicated above, the screw and wedge and bone-piercing device can be welded together or press fit or otherwise fixed together in any desired way such as welding at the bolt 26 in the wedge and bone anchor 122 and the hole 83H in the wedge.

In the FIG. 26 installation, like those in FIGS. 7A, 7B, 19A and 19B, the curved anterior edge 83A of the wedge 83 conforms to the anterior perimeter of the vertebral body at the osteotomy site. The shape of the posterior edge 83P, and the proximity of the edge 83P to the screw axis, assure avoidance of the spinal foramen.

Figure 27:
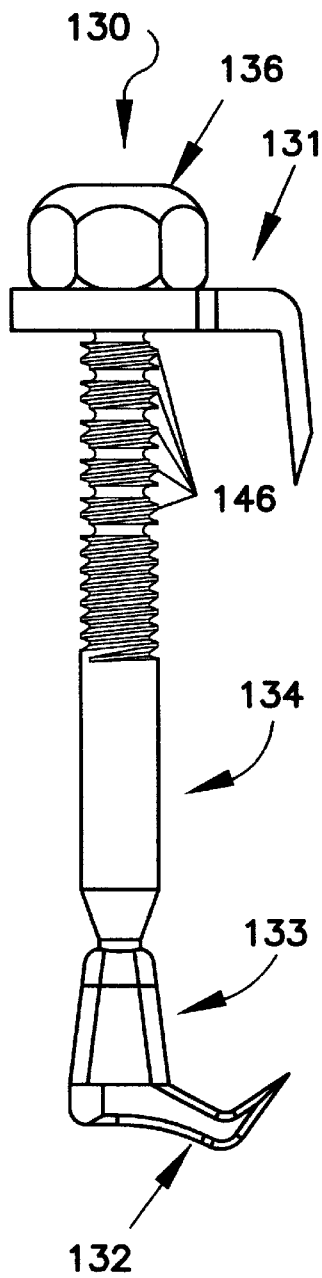
FIG. 27 is an elevational view of another embodiment of the correction device.
Figure 29:
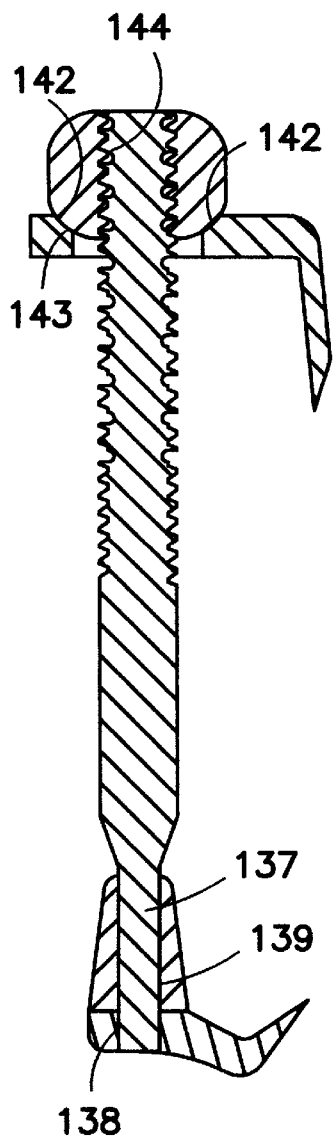
FIG. 29 is a section therethrough taken at line 29—29 in FIG. 8 and viewed in the direction of the arrows.
Figure 28:
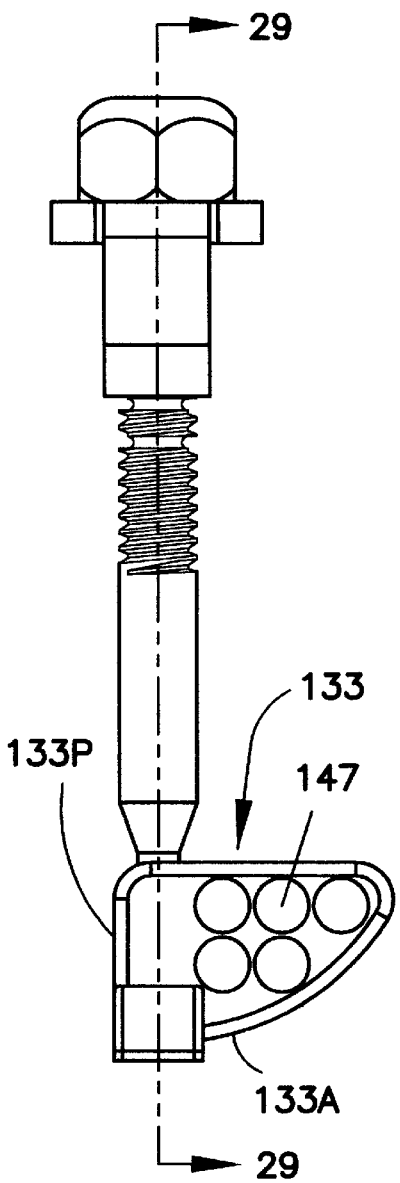
FIG. 28 is another elevational view of the device of FIG. 27 rotated on its axis 90°.

Referring now to FIGS. 27 through 29, this embodiment of the instrumentation is proposed for those cases in which the spinal deformity is sufficiently mild that reasonable correction can be obtained by opening wedge osteotomies, but without intervertebral connection. In this connection device 130, there is the bone piercing device 131 virtually identical to device 121 in FIG. 20. It is received on the screw 134 which has the lower bone piercing device 132 at the lower end, wedge 133 immediately above it, and a head 136 at the top. The lower bone piercing device 132 serves as an anchor in basically the same manner as described above with reference to FIG. 26 and is welded to the lower end 137 of the screw as at 138, for example. The wedge 133 may be welded to the screw at 139 or to the anchor 132.

The upper bone piercing device 131 has a central aperture 141 with a chamfer 142 at the upper edge of the opening on which is a convex surface 143 (typically spherical) of the head 136 is bearing when the head is screwed onto threads 146 with which the internal threads 144 of the head are mated. As described with reference to previous embodiments, the spaces between thread sets are narrowed so that, after installation of the connection device, and depending upon the distance between the two anchors, a portion of the upper end of the screw may extend beyond the top of the head 36 and can be broken off to provide a flush surface as shown in FIGS. 27 through 29.

As shown in FIG. 28, the wedge is shaped so that the anterior edge 133 will somewhat conform to the shape of the intervertebral body as shown for the wedge 83 in FIG. 19B for that embodiment of the invention. Also, the posterior edge 133P of wedge 133 is close to the longitudinal axis of the screw to adequately space it from the spinal foramen. Apertures 147 in the wedge are provided for the same reason as discussed above.

Figure 30:
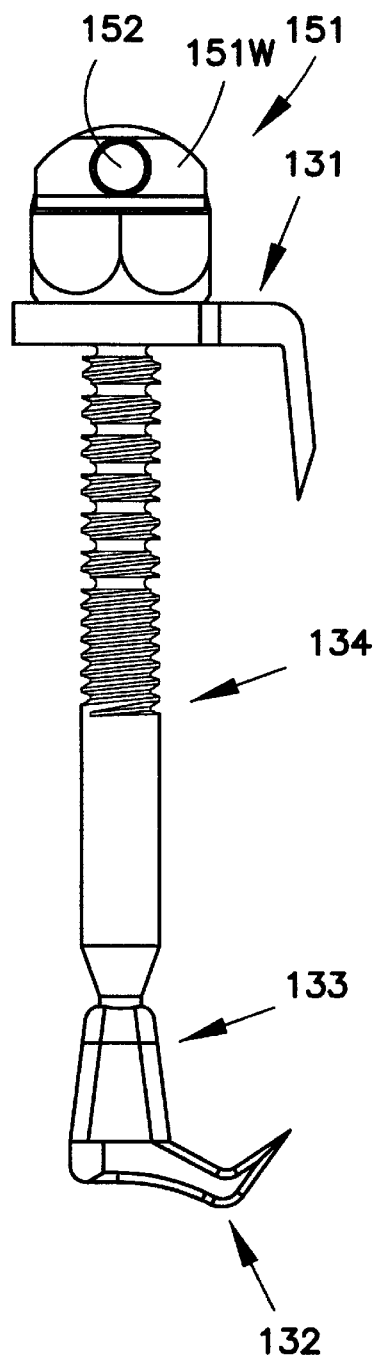
FIG. 30 is a elevational view of still a further embodiment of the invention useful in a tethering application.
Figure 32:
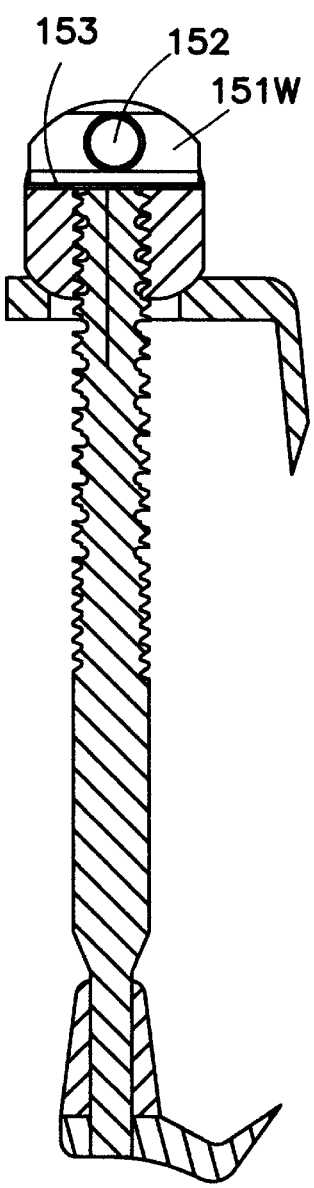
FIG. 32 is a section therethrough taken at line 32—32 in FIG. 31 and viewed in the direction of the arrows.
Figure 31:
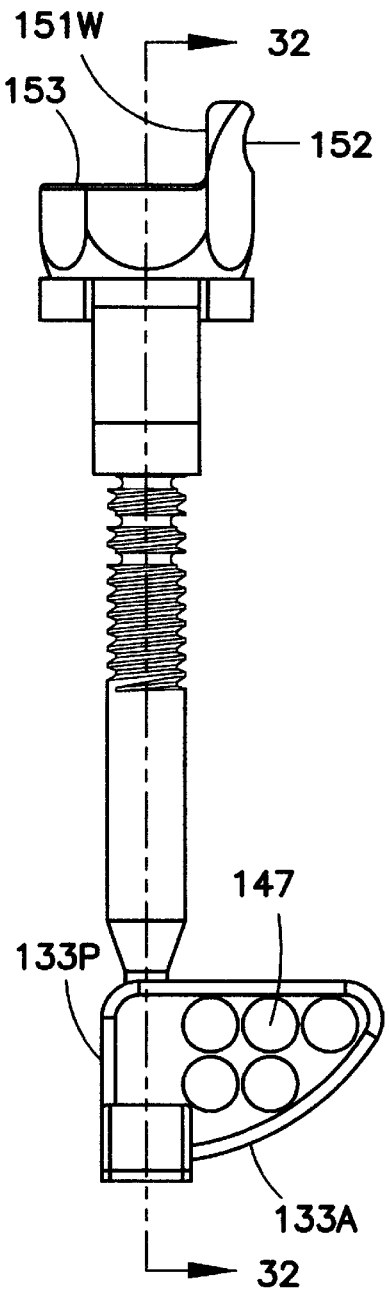
FIG. 31 is an elevational view thereof with the device turned 90° on its axis.

Referring now to FIGS. 30 through 32, all features of this embodiment are the same as in the previously described embodiment except for the head. In this embodiment, while the head 151 has an external hexagonal surface as in the previously described embodiment, it is slightly different in the respect that the head is larger in a radial dimension with respect to the axis of the screw 134. It also has a wall 151W radially spaced from the screw axis and which has an aperture 152 through it. it. This embodiment of the present invention is intended for use in those applications where a metal cable or plastic tether such as of braided polyethylene may be used to make connections between the instrumentation of this type in one vertebral body, and that in another vertebral body. Such connections may be made between adjacent vertebral bodies, or vertebral bodies that are spaced from each other with other vertebral bodies in the space. As in the previously described embodiment, depending upon the distance of the anchors 131 and 132 after the instrumentation is installed in the vertebral body, if any portion of the upper end of the screw 134 extends above the shelf 153 of the head, that portion of the screw can be broken off.

It should be understood from the foregoing description of the embodiments of FIGS. 27 through 31, that the procedure for use is much the same as that described above with reference to FIGS. 15 through 26.

The present invention provides a surgical technique that permits correction of spinal deformities without the need for fusion of the intervertebral discs. The osteotomies conducted according to the technique can be done rapidly using conventional instruments while still protecting the spinal cord and controlling bleeding. The use of staples on opposite sides of the vertebral body maintain the osteotomy sites in their required configuration for bone union to occur. Ancillary support for the instrumented vertebrae can be provided by way of a removable elongated member spanning the spine, such as a spinal rod. Unlike prior techniques in which fusion of the disc space is performed, the spinal rod need not bear as much of the spinal loads as in the other procedures. Thus, the rod can have a smaller diameter than traditional spinal instrumentation rods. An ultimate goal of the present invention is removal of the spinal rod once bone union has occurred at the osteotomy site. The present invention contemplates application to a wide variety of spinal deformities, although correction of scoliosis may be a principal application.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. An apparatus for use in the correction of spinal deformities, comprising:

a first anchor having at least one prong configured to penetrate one side of a vertebral body of a vertebra to be corrected; and a second anchor having at least one prong configured to penetrate an opposite side of said vertebral body of the vertebra to be corrected;

means for extending through said vertebral body for pulling said first anchor toward said second anchor when said anchors penetrate said vertebral body on substantially opposite sides of said vertebral body.

2. The apparatus of claim 1 and wherein:

each of said anchors has another prong, and is a staple.

3. The apparatus of claim 1, wherein said means for pulling said first anchor toward said second anchor includes:

an elongate member having a longitudinal axis and sized to extend through the vertebral body and between the opposite sides of the vertebral body, said member having one end and an opposite end and having a wedge extending from said first anchor and a threaded shank extending from the opposite end; and a head threaded onto said shank, said second anchor defining an opening therethrough smaller than said head.

4. The apparatus of claim 3, wherein said second anchor is L-shaped, having a proximal portion with said opening centered on said axis, with said prong having a first portion extending radially from said proximal portion and said prong having a second portion spaced from said axis and extending generally parallel to said axis, toward said first anchor and having a sharp distal end to penetrate said vertebral body.

5. The apparatus of claim 3 wherein:

said head has a convex lower surface engaging said second anchor.

6. The apparatus of claim 5 wherein:

said head has a hexagonal tool-receiver outer surface.

7. The apparatus of claim 5 wherein:

said second anchor has a sloped surface engaged by said convex surface of said head.

8. The apparatus of claim 3 wherein:

said head has a receiver aperture therethrough for a flexible connector.

9. The apparatus of claim 8 wherein:

the receiver aperture has an axis generally transverse to said longitudinal axis.

10. The apparatus of claim 9 wherein:

said head has a tool receiver surface thereon engageable by an external tool for installing said head on said shank; and said head has a wall extending generally parallel to the said longitudinal axis of said elongate member; and said wall has said aperture therethrough for reception of a cable therethrough.

11. The apparatus of claim 10 wherein:

said tool receiver surface is hexagonal.

12. The apparatus of claim 3 wherein:

said second anchor has a second prong configured to penetrate said opposite side of said vertebral body;

said second anchor having a proximal portion with said opening centered on said axis, and with each of said prongs having first portions extending radially from said proximal portion and said prongs having distal portions spaced from said axis and extending generally parallel to said axis toward said first anchor and having a sharp distal end to penetrate said vertebral body.

13. The apparatus of claim 3, wherein said head defines a circumferential surface for engaging said second anchor adjacent said opening.

14. The apparatus of claim 3, wherein said head defines a channel therethrough for receiving an elongate rod therein.

15. The apparatus of claim 3 wherein:

said threaded shank includes a plurality of spaced sets of external threads for mating with said head, said sets of threads being spaced along the shank from the opposite end and having reduced cross sectional areas between the sets and adopted to breaking away a length of the shank extending from the opposite end toward the one end at a location selected to clear the channel for admission of said elongate rod.

16. The apparatus of claim 15 and further comprising:

a set screw, operable to secure said rod in said channel;

the head having threads spaced from said shank and threadedly receiving said set screw in said head.

17. The apparatus of claim 16 and wherein:

said set screw is a break-off set screw.

18. The apparatus of claim 1, wherein:

said means for pulling said first anchor toward said second anchor includes an elongate member having a longitudinal axis and sized to extend through the vertebral body and between the opposite sides of the vertebral body; and said first anchor has a proximal portion connected to one end of said elongate member, and said one prong has a first portion projecting radially outward from said proximal portion and away from said second anchor to a location radially spaced from said elongate member, and said one prong has a second portion turning from said first portion toward said second anchor and terminating at a sharp distal end.

19. The apparatus of claim 18 wherein:

said second portion of said one prong has surfaces beginning at said location of said turning from said first portion and converging to said sharp distal end.

20. The apparatus of claim 1 and wherein said means for pulling said first anchor toward said second anchor includes an elongate member having a longitudinal axis and sized to extend through the vertebral body and between the opposite sides of the vertebral body;

said first anchor has a proximal portion connected to one end of said elongate member, and said one prong has a first portion projecting radially outward from said proximal portion and away from said second anchor to a location radially spaced from said elongate member and said one prong has a second portion turning toward said second anchor and terminating at a sharp distal end;

said first anchor has a second prong which has a first portion projecting radially outward from said proximal portion and away from said second anchor to a location radially spaced from said elongate member, and said second prong has a second portion turning toward said second anchor and terminating at a sharp distal end.

21. The apparatus of claim 20 and wherein:

said first and second portions of said first and second prongs combine with said proximal portion connected to said one end of said elongate member whereby said first anchor has an inverted gull wing configuration.

22. The apparatus of claim 1, wherein said means for pulling said first anchor toward said second anchor includes:

an elongate member having a longitudinal axis and sized to extend through the vertebral body and between the opposite sides of the vertebral body, said member having one end and an opposite end and having a wedge at the one end and a head at the opposite end;

the wedge being configured to fill at least a portion of an osteotomy site in the vertebral body.

23. The apparatus of claim 22 wherein:

the wedge has angled faces and first and second oppositely-facing ends, one of the ends being shaped to conform to the shape of a portion of the perimeter of the vertebral body at the osteotomy site.

24. The apparatus of claim 23 wherein:

the other of the ends of the wedge is located proximate the axis of the elongate member to avoid the spinal foramen of the vertebral body.

25. The apparatus of claim 22 wherein:

said wedge has a plurality of apertures therein to enable vertebral tissue to grow through said apertures.

26. The apparatus of claim 25 and wherein:

the elongate member is a threaded shank having threads thereon threadedly engaging at least one of the wedge or the head.

27. The apparatus of claim 26 wherein:

said first anchor has a proximal portion connected to one end of said elongate member, and said one prong has a first portion projecting radially outward from said proximal portion and away from said second anchor to a location radially spaced from said elongate member and said one prong has a second portion turning toward said second anchor and terminating at a sharp distal end;

said first anchor has a second prong which has a first portion projecting radially outward from said proximal portion and away from said second anchor to a location radially spaced from said elongate member, and said second prong has a second portion turning toward said second anchor and terminating at a sharp distal end, whereby said first anchor has a shape that generally conforms to the concave profile of the vertebral body.

28. The apparatus of claim 27 wherein:

said second anchor has a second prong configured to penetrate said opposite side of said vertebral body;

said second anchor having a proximal portion with said opening centered on said axis, and with each of said prongs of said second anchor having first portions extending radially from said proximal portion and said prongs having distal portions spaced from said axis and extending generally parallel to said axis toward said first anchor and having a sharp distal end to penetrate said vertebral body.

29. The apparatus of claim 28 and wherein:

said first and second portions of said first and second prongs of said first anchor combine with said proximal portion connected to said one end of said elongate member whereby said first anchor has a wide 'W' configuration.

30. An apparatus for use in the correction of spinal deformities, comprising:

first and second anchor members configured to engage respective opposite sides of a vertebral body; and a connector member coupled to each of said first and second anchor members and extending through an interior portion of the vertebral body, said connector member adapted to pull said first anchor member toward said second anchor member to engage said first and second anchor members to said respective opposite sides of the vertebral body.

31. The apparatus of claim 30, wherein each of said first and second anchor members is a staple.

32. The apparatus of claim 31, wherein said staple has at least two prongs configured to engage the vertebral body.

33. The apparatus of claim 32, wherein said at least two prongs include sharp distal ends configured to penetrate the vertebral body.

34. The apparatus of claim 30, wherein said connector member comprises an elongate member having opposite end portions extending along an axis, one of said end portions including a wedge configured to fill at least a portion of an osteotomy site in the vertebral body.

35. The apparatus of claim 34, wherein said wedge has angled faces and first and second oppositely-facing ends, one of said oppositely-facing ends being shaped to conform to the shape of a peripheral portion of the vertebral body at the osteotomy site.

36. The apparatus of claim 35, wherein the other of said oppositely-facing ends of said wedge is located proximate the axis of said elongate member to avoid the spinal foramen of the vertebral body.

37. The apparatus of claim 34, wherein said wedge has a plurality of apertures therein to enable in-growth of vertebral tissue.

38. The apparatus of claim 34, wherein said elongate member includes a threaded shank configured to threadedly engage a corresponding threaded portion of said wedge.

39. An apparatus for use in the correction of spinal deformities, comprising:

a first bone piercing device positioned adjacent one side of a vertebral body;

a second bone piercing device positioned adjacent an opposite side of the vertebral body; and an elongate member extending through an interior portion of the vertebral body and coupled to each of said first and second bone piercing devices, said elongate member adapted to provide a compressive force on the vertebral body between said first and second bone piercing devices.

40. The apparatus of claim 39, wherein each of said first and second bone piercing devices is a staple.

41. The apparatus of claim 40, wherein said staple has at least two prongs configured to engage the vertebral body.

42. The apparatus of claim 39, wherein each of said first and second bone piercing devices includes at least one sharp distal end configured to penetrate the vertebral body.

43. An apparatus for use in the correction of spinal deformities, comprising:

first and second anchor members configured to engage opposite sides of a vertebral body; and an elongate member extending through an interior portion of the vertebral body and coupling said first anchor member to said second anchor member, said elongate member having a threaded portion configured to threadedly engage a corresponding threaded portion of said first anchor member to pull said first anchor member toward said second anchor member and to engage said first and second anchor members against said opposite sides of the vertebral body.

44. The apparatus of claim 43, wherein each of said first and second anchor members is a staple.

45. The apparatus of claim 44, wherein said staple has at least two prongs configured to engage the vertebral body.

46. The apparatus of claim 45, wherein said at least two prongs include sharp distal ends configured to penetrate the vertebral body.

\* \* \* \* \*